(12) United States Patent
Van Deventer et al.

(10) Patent No.: US 8,119,401 B2
(45) Date of Patent: Feb. 21, 2012

(54) IL-10 GENE TRANSFER TO PERIPHERAL MONONUCLEAR CELLS

(75) Inventors: Sander Jan Hendrik Van Deventer, Haarlem (NL); Catherine Van Montfrans, Amsterdam (NL)

(73) Assignee: Amsterdam Molecular Therapeutics (AMT) IP B.V., Amsterdam Zuidoost (NL)

( * ) Notice: Subject to any disclaimer, the term of this patent is extended or adjusted under 35 U.S.C. 154(b) by 0 days.

(21) Appl. No.: 10/506,881

(22) PCT Filed: Mar. 7, 2003

(86) PCT No.: PCT/NL03/00170
§ 371 (c)(1),
(2), (4) Date: Oct. 5, 2005

(87) PCT Pub. No.: WO03/074685
PCT Pub. Date: Sep. 12, 2003

(65) Prior Publication Data
US 2007/0053889 A1   Mar. 8, 2007

(30) Foreign Application Priority Data
Mar. 7, 2002   (EP) .................................... 02075895

(51) Int. Cl.
*A61K 48/00* (2006.01)
*C12N 5/071* (2010.01)
*C12N 5/0783* (2010.01)

(52) U.S. Cl. .... 435/372; 435/69.5; 435/325; 435/372.3; 435/377; 424/93.21

(58) Field of Classification Search .................. 435/325, 435/455; 424/93.1
See application file for complete search history.

(56) References Cited

U.S. PATENT DOCUMENTS 6,540,999 B1 *   4/2003   Harn et al. .................. 424/184.1
6,692,964 B1 *   2/2004   June et al. ...................... 435/455

OTHER PUBLICATIONS

Takayama et al., Transplantation. May 15, 2001;71(9):1334-1340.*
Setoguchi et al., *Antigen-Specific T Cells Transduced with IL-10 Ameliorate Experimentally Induced Arthritis Without Impairing the Systemic Immune Response to the Antigen*, Journal of Immunology, The Williams and Wilkins Co., Baltimore, vol. 165, No. 10. Nov. 15, 2000, pp. 5980-5986.
Moritani, et al., *Prevention of Adoptively Transferred Diabetes in Nonobese Diabetic Mice with IL-10-Transduced Islet-specific Th1 Lymphocytes: A gene therapy model for autoimune diabetes*, Journal of Clinical Investigtion, New York, NY, US, vol. 98, No. 8, 1996, pp. 1851-1859.
Mathisen, et al., *Treatment of Experimental Autoimmune Encephalomyelitis with Genetically Modified Memory T Cells*, Journal of Experimental Medicine, vol. 186, No. 1, 1997, pp. 159-164.
Asseman, et al., *An Essential Role for Interleukin 10 in the Function of Regulatory T Cells That Inhibit Intestinal Inflammation*, Journal of Experimental Medicine, vol. 190, No. 7, Oct. 4, 1999, pp. 995-1003.
Hagenbaugh, et al., *Altered Immune Responses in Interleukin 10 Transgenic Mice*, The Journal of Experimental Medicine, United States, Jun. 16, 1997, vol. 185, No. 12, pp. 2101-2110.
Mavilio, et al., *Peripheral Blood Lymphocytes as Target Cells of Retroviral Vector-Mediated Gene Transfer*, Blood, United States, Apr. 1, 1994, pp. 1988-1997.
Groux, et al, *Regulatory T cells and Inflammatory Bowel Disease*, Immunology Today, Elsevier Publications, Cambridge, vol. 20, No. 10, Oct. 1, 1999, pp. 442-445.
Van Montfrans, et al., *Generation of Regulatory Gut-Homing Human T Lymphocytes Using Ex Vivo Interleukin 10 Gene Transfer*, Gastroenerology, vol. 123, No. 6, Dec. 20, 2002, pp. 1877-1888.
Madsen, *Combining T cells and IL-10: A New Therapy for Crohn's Disease?*, Gastroenterology, vol. 123, No. 6, Dec. 20, 2002, pp. 2140-2144.
*Notification of Transmittal of the Internatinal Preliminary Examination Report; Internatioal Preliminary Examination Report*, PCT, Jun. 16, 2004.
International Search Reoprt, PCT, Aug. 27, 2003.

* cited by examiner

*Primary Examiner* — Daniel C Gamett
(74) *Attorney, Agent, or Firm* — Browdy and Neimark, PLLC

(57) ABSTRACT

The present invention to methods for producing mononuclear cells overexpressing IL-10. The method comprises the ex vivo introduction of an expression construct comprising a nucleotide sequence encoding a polypeptide having IL-10 activity into peripheral blood mononuclear cells of a subject. The thus obtained peripheral blood mononuclear cells have an altered phenotype as a result of the expression of an introduced IL-10 transgene. In particular the invention relates to CD4+ T cells that functionally behave as regulatory T cells as a result of the expression of an IL-10 transgene. The IL-10 transgenic mononuclear cells may be used to treat a variety of inflammatory diseases, particularly T helper 1-mediated inflammatory diseases.

21 Claims, 12 Drawing Sheets

SEQUENCE LISTING

```
<160> NUMBER OF SEQ ID NOS: 2

<210> SEQ ID NO 1
<211> LENGTH: 178
<212> TYPE: PRT
<213> ORGANISM: Homo sapiens

<400> SEQUENCE: 1

Met His Ser Ser Ala Leu Leu Cys Cys Leu Val Leu Leu Thr Gly Val
  1               5                  10                  15

Arg Ala Ser Pro Gly Gln Gly Thr Gln Ser Glu Asn Ser Cys Thr His
                 20                  25                  30

Phe Pro Gly Asn Leu Pro Asn Met Leu Arg Asp Leu Arg Asp Ala Phe
             35                  40                  45

Ser Arg Val Lys Thr Phe Phe Gln Met Lys Asp Gln Leu Asp Asn Leu
 50                  55                  60

Leu Leu Lys Glu Ser Leu Leu Glu Asp Phe Lys Gly Tyr Leu Gly Cys
 65                  70                  75                  80

Gln Ala Leu Ser Glu Met Ile Gln Phe Tyr Leu Glu Glu Val Met Pro
                 85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 2
```

```
-continued

<211> LENGTH: 170
<212> TYPE: PRT
<213> ORGANISM: Homo sapiens

<400> SEQUENCE: 2

Met Glu Arg Arg Leu Val Val Thr Leu Gln Cys Leu Val Leu Leu Tyr
 1               5                  10                  15

Leu Ala Pro Glu Cys Gly Gly Thr Asp Gln Cys Asp Asn Phe Pro Gln
                20                  25                  30

Met Leu Arg Asp Leu Arg Asp Ala Phe Ser Arg Val Lys Thr Phe Phe
            35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ala Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170
```

IL-10 GENE TRANSFER TO PERIPHERAL MONONUCLEAR CELLS

FIELD OF THE INVENTION

The present invention relates to peripheral blood mononuclear cells having an altered phenotype as a result of the expression of an introduced IL-10 transgene. The invention further relates to methods for obtaining such IL-10 transgenic mononuclear cells. In particular the invention relates to CD4+ T cells that functionally behave as regulatory T cells as a result of the expression of an IL-10 transgene. The IL-10 transgenic mononuclear cells may be used to treat a variety of inflammatory diseases, particularly T helper 1-mediated inflammatory diseases.

BACKGROUND OF THE INVENTION

The qualitative characteristics of the immune responses are regulated by T cell subsets through their production of distinctive cytokines. Well-characterised T cell subsets are T helper (Th) cells, of which two different subsets are recognised. Th1 cells, which through the production of IFN-γ, promote cell-mediated responses, and Th2 cells which, by producing IL-4, IL-5, IL-13, induce antibody synthesis, as well as mast cell and eosinephil responses. Both subsets originate from a naive T cell precursor, whose differentiation is influenced by both the modes of activation and the environment. A number of variables known to influence the development of T cell subsets includes the interaction of the T cell receptor (TCR) with antigen, the presence of antigen presenting cells (APC) and the presence of certain cytokines during activation of the T cells.

A third subset of T cells, so-called regulatory CD4+ cells or regulatory T cells, is described that predominantly produces interleukin-10 (IL-10)[1]. IL-10 inhibits a broad array of immune parameters, including activation and effector function of T cells, monocytes and dendritic cells (DCs), limiting and ultimately terminating inflammatory responses[2, 3]. These IL-10 producing T cells are named regulatory T cells type 1 (Tr1), because of their immunosuppressive effects both in vitro[4] and in experimental colitis[1]. Tr1 cells produce little IL-2, no IL-4 and the production rate of IL-5, IFN-γ and transforming growth factor beta (TGF-β) is similar to those of naïve T cell clones. The mechanisms by which regulatory T cells mediate immunosuppressive activities in vivo are still unknown, but some regulatory T cell populations are known to be dependent on IL-10 for their function[5, 6].

Studies of IL-10 deficient (IL-10−/−) and IL-10 receptor-2 deficient mice[7, 8], which show that these mice develop a T helper (Th)-1 mediated intestinal inflammation in the absence of IL-10 or IL-10 mediated signalling indicate that IL-10 is an important regulatory cytokine within the mucosal immune system. The activity of IL-10 in counter regulating mucosal inflammation is likely to be multifactorial. IL-10 is a potent down regulator of IL-12 production and thus acts at the level of Th1 cell induction.[9] In addition, IL-10 suppresses production of other proinflammatory cytokines and chemokines including TNF-α, IL-1, IL-6 and IL-8.[3] Finally, there is substantial evidence that IL-10 acts both to promote the differentiation and augment the activity of regulatory T cells.[1, 6, 10, 11]

The observations in IL-10−/− mice have laid the foundation for therapeutic trials of IL-10 in several other models of colitis. These studies have shown that systemic IL-10 administration is able to prevent intestinal inflammation by down-regulating the intestinal proinflammatory Th1 response.[7, 12, 13] Based on these successful experimental findings, recombinant (r)IL-10 was administered by subcutaneous injection to patients with either mild/moderate or steroid refractory Crohn's disease, as well as in patients undergoing ileal resection to prevent postoperative recurrence.[14-16] Although the data indicated that systemic rIL-10 therapy is safe and well tolerated, this therapy did not result in significantly higher remission rates or clinical improvement compared to placebo. Explanations for this lack of efficacy include the short half-life of rIL-10,[17] local delivery of insufficient amounts of rIL-10 to inhibit mucosal Th1 responses and the side effects associated with high dose rIL-10.[18] Sustained IL-10 delivery may prove more effective than daily systemic injections.

These limitations of systemic rIL-10 therapy might be overcome by the infusion of in vitro generated regulatory T cells to patients with T cell-mediated inflammatory diseases. However, the low proliferation rate of regulatory T cells and the high cost of rIL-10, required for their generation in vitro, seriously hamper the production in vitro of therapeutically effective quantities of regulatory T cells.

In an experiment to overcome the anti-proliferative properties of IL-10, antigen-specific murine T cells transduced with IL-10 have been employed (Setoguchi et al., 2000, J. Immunol. 165: 5980-5986). Splenic T cells from mice transgenic for an ovalbumin-specific TCR were transduced with a retroviral plasmid containing the murine IL-10 gene. The IL-10-transduced ovalbumin-specific T cells were subsequently infused into mice with antigen (ovalbumin) induced arthritis. The transduced T cells migrated to the inflamed joint and ameliorated the arthritis symptoms of the joint. However, this use of IL-10 transduced T cells is strictly limited to T cells that are specific for a predetermined antigen. As for most (if not all) inflammatory diseases the relevant antigens are not known, this antigen-specific application of IL-10-expressing T cells currently has no practical therapeutic value.

In experimental autoimmune encephalomyelitis (EAE), a Th1 mediated disease, efficient delivery to the site of inflammation of either therapeutic[19] or exacerbating factors[20] by genetically modified T cells has been reported. Encouraging results were obtained from a study showing that antigen specific T-cell clones transfected with IL-10 cDNA were able to inhibit EAE[19] However, because of the antigen specificity of the transfected T cell clones these results again have no practical therapeutic value.

Thus, it is an object of the invention to provide for IL-10 producing regulatory T cells for use in the therapy of inflammatory diseases in an antigen-independent manner, as well as to provide for methods of obtaining such regulatory T cells. In general, it is an object of the invention to provide for mononuclear cell populations that are derived from peripheral blood mononuclear cells (PBMCs) and that are transgenic for IL-10. Such IL-10 transgenic mononuclear cell populations or specific subfractions thereof may be used as therapeutic agents in a variety of inflammatory diseases, in particular in Th1-mediated inflammatory diseases.

DESCRIPTION OF THE INVENTION

Definitions

IL-10 Polypeptides

An "IL-10 polypeptide" or "IL-10" is herein defined as a polypeptide having IL-10 activity and encompasses any naturally occurring or recombinant polypeptides capable of specifically binding an IL-10 receptor and effecting a response to IL-10. Polypeptide having IL-10 activity are also referred as cytokine synthesis inhibitory factor (CSIF). Nucleotide sequences encoding polypeptides having IL-10 activity that are useful in the present invention include fragments, mutated forms, or modified polypeptides as described in detail in U.S. Pat. No. 5,231,012, U.S. Pat. No. 6,319,493 or WO91/00349, which are incorporated herein by reference. Polypeptides having IL-10 activity exhibit several biological activities, which may form the basis of assays and units (see, e.g., Moore, et al. (1993) Ann. Rev. Immunol. 11:165-190). Assays for determining IL-10 activity are described in e.g. U.S. Pat. No. 6,319,493 and include e.g. assays based on the IL-10 property of inhibiting the synthesis of at least one cytokine in the group consisting of IFN-γ, lymphotoxin, IL-2, IL-3, and GM-CSF in a population of T helper cells induced to synthesise one or more of these cytokines by exposure to syngeneic antigen presenting cells (APCs) and antigen. In this activity, the APCs are treated so that they are incapable of replication, but their antigen processing machinery remains functional. This is conveniently accomplished by irradiating the APCs, e.g., with about 1500-3000 R (gamma or X-radiation) before mixing with the T cells. In an alternative IL-10 activity assay, cytokine inhibition may be determined in primary or, preferably, secondary mixed lymphocyte reactions (MLR), in which case syngeneic APCs need not be used. MLRs are well known in the art, see, e.g., Bradley, pp. 162-166, in Mishell, et al. (eds.) (1980) Selected Methods in Cellular Immunology, Freeman, San Francisco; Battisto, et al. (1987) Meth. in Enzymol. 150:83-91; and Coligan et al. (eds.) (1991 and periodic supplements).[21]

Briefly, two populations of allogenic lymphoid cells are mixed, one of the populations having been treated prior to mixing to prevent proliferation, e.g., by irradiation. Preferably, the cell populations are prepared at a concentration of about $2*10^6$ cells/ml in supplemented medium, e.g., RPMI 1640 with 10% fetal calf serum. For both controls and test cultures, mix 0.5 ml of each population for the assay. For a secondary MLR, the cells remaining after 7 days in the primary MLR are re-stimulated by freshly prepared, irradiated stimulator cells. The sample suspected of containing IL-10 may be added to the test cultures at the time of mixing, and both controls and test cultures may be assayed for cytokine production or cell proliferation from 1 to 3 days after mixing (Coligan, 1994 #4745).

Nucleotide Sequences Encoding IL-10

A nucleotide sequence encoding an IL-10 polypeptide is herein defined as any nucleotide sequence that encodes a polypeptide having IL-10 activity as defined above. The nucleotide sequence preferably encodes a IL-10 polypeptide having an amino acid sequence with at least 65% amino acid identity with amino acids 19 to 178 of SEQ ID NO. 1 or with amino acids 24 to 170 of SEQ ID NO. 2, i.e. the mature forms of these IL-10 polypeptides. These two forms of IL-10 are sometimes referred to as human IL-10 (or human cytokine synthesis inhibitory factor ("CSIF") and viral IL-10 (or BCRF1), respectively, e.g., Moore, et al., Science 248:1230-1234 (1990); Vieira, et al., Proc. Natl. Acad. Sci. 88:1172-1176 (1991); Fiorentino, et al., J. Exp. Med. 170:2081-2095 (1989); and Hsu, et al., Science 250:830-832 (1990). Other suitable nucleotide sequences encoding polypeptides having IL-10 activity include e.g. an IL-10 homologue as described in equine herpesvirus type 2 (Roe, et al., Virus Genes 7:111-116 (1993)), as well as numerous counterparts from various species.

The amino acid identity between a polypeptide comprised in the term "Polypeptide having IL-10 activity" and SEQ ID NO. 1 or SEQ ID NO. 2 may be readily calculated by known methods, including but not limited to those described in (Computational Molecular Biology, Lesk, A. M., ed., Oxford University Press, New York, 1988; Biocomputing: Infomatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). Preferred methods to determine identity are designed to give the largest match between the sequences tested. Methods to determine identity are codified in publicly available computer programs. Preferred computer program methods to determine identity and similarity between two sequences include, but are not limited to, the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410(1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity. Preferred parameters for polypeptide sequence comparison include the following: 1) Algorithm: Needleman and Wunsch, J. Mol. Biol. 48:443-453 (1970) Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for peptide comparisons (along with no penalty for end gaps).

Alternatively, nucleotide sequences encoding polypeptide having IL-10 activity may be defined by their capability to hybridise with (the complementary strands of) nucleotide sequences encoding any of the amino acid sequences of SEQ ID NO. 1 or SEQ ID NO. 2, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity. Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

Homologous

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species.

When used to indicate the relatedness of two nucleic acid sequences the term "homologous" means that one single-stranded nucleic acid sequence may hybridise to a complementary single-stranded nucleic acid sequence. The degree of hybridisation may depend on a number of factors including the amount of identity between the sequences and the hybridisation conditions such as temperature and salt concentration as discussed above. Preferably the region of identity is greater than about 5 bp, more preferably the region of identity is greater than 10 bp.

Autologous

The term "autologous" is used herein to refer to proteins, nucleic acids, cells, tissues or organs that are obtained from one subject or patient and that are, preferably after some form of ex vivo treatment, returned to, administered to or reinplanted or reinfused into the same subject or patient.

Promoter

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated. A "tissue specific" promoter is only active in specific types of tissues or cells.

Operably Linked

As used herein, the term "operably linked" refers to two or more nucleic acid or amino acid sequence elements that are physically linked in such a way that they are in a functional relationship with each other. For instance, a promoter is operably linked to a coding sequence if the promoter is able to initiate or otherwise control/regulate the transcription and/or expression of a coding sequence, in which case the coding sequence should be understood as being "under the control of" the promoter. Generally, when two nucleic acid sequences are operably linked, they will be in the same orientation and usually also in the same reading frame. They will usually also be essentially contiguous, although this may not be required.

Signal Sequence

The terms "signal sequence", "signal peptide" and "secretory leader" are used interchangeably and refer to a short (usually about 15-60 amino acids), continuous stretch of amino acids usually present at the amino-terminus of secreted and membrane-bound polypeptides and that directs their delivery to various locations outside the cytosol. Thus, specific sorting or targeting signals, which include signal sequences, may direct the delivery of polypeptides into the nucleus, ER, mitochondria, peroxisomes, etc. Signal sequences usually contain a hydrophobic core of about 4-15 amino acids, which is often immediately preceded by a basic amino acid. At the carboxyl-terminal end of the signal peptide there are a pair of small, uncharged amino acids separated by a single intervening amino acid that defines the signal peptide cleavage site. von Heijne, G. (1990) J. Membrane Biol. 115: 195-201. Despite their overall structural and functional similarities, native signal peptides do not have a consensus sequence.

Transgene

A "transgene" is herein defined as a gene that has been newly introduced into a cell, i.e. a gene that does not normally occur in the cell. The transgene may comprise sequences that are native to the cell, sequences that in naturally do not occur in the cell and it may comprise combinations of both. A transgene may contain sequences coding for one or more proteins that may be operably linked to appropriate regulatory sequences for expression of the coding sequences in the cell.

DETAILED DESCRIPTION OF THE INVENTION

The present invention is based on the surprising discovery that $CD4^+$ T cells present in populations of peripheral blood mononuclear cells (PBMCs) can be phenotypically altered ex vivo by transduction with a retroviral vector capable of expressing IL-10. The IL-10 expression confers to the transduced $CD4^+$ T cells a regulatory function that mimics the immunosuppressive function of Tr1 cells. The IL-10 transduced $CD4^+$ T cells may be formulated into pharmaceutical compositions for infusion into subjects suffering from an inflammatory disease to control the inflammation. In view of the central role of IL-10 in immunosuppression and control of inflammation, these findings can be extended to other subfractions or cell types present in PBMCs, such as of lymphocytes, B cells, T cells, $CD4^+$ cells, macrophages, monocytes or dendritic cells. The introduction of IL-10 expression from a transgene in the cell types may be used to alter the phenotype of the cells ex vivo, preferably in an antigen independent manner. Alternatively, the transgenic IL-10 expressing cells or specific subsets thereof may be used as vehicles to deliver in situ IL-10 production to specific (inflamed) areas in the body. Thus, in its broadest sense the present invention relates to a mononuclear cell that expresses IL-10 from a transgene, whereby the expression of IL-10 from the transgene produces at least one phenotypic alteration in the mononuclear cell as compared to a non-transgenic counterpart of the cell, as well as, to methods for producing such IL-10 transgenic mononuclear cells.

In a first aspect the invention therefore relates to a method for producing mononuclear cells overexpressing IL-10, wherein the method comprises the steps of: (a) providing a composition comprising PBMCs; (b) introducing an expression construct comprising a nucleotide sequence encoding a polypeptide having IL-10 activity into at least part of the mononuclear cells; and, (c) recovery of mononuclear cells overexpressing IL-10.

The composition comprising PBMCs preferably is obtained from a mammal, more preferably from a human (individual). Preferably the composition comprising PBMCs is obtained from a mammalian subject suffering from an inflammatory disease such as e.g. a Th1-mediated inflammatory disease as described below. Preferably the composition comprising PBMCs is obtained from a single mammalian individual so that after application of the method of the invention, the transgenic mononuclear cells are suitable for autologous infusion or adoptive transfer. The composition of PBMCs is preferably not obtained from a non-human mammal that is transgenic for an homologous or heterologous IL-10 gene.

The composition comprising PBMCs may be obtained from the mammal using a variety of methods well known in the art (see e.g. Coligan, 1994 #4746). The composition comprising PBMCs may e.g. consist of the PBMC bulk that is obtainable by aphaeresis, Ficoll density gradient centrifugation and/or red blood cell lysis from mammalian blood. For higher yields of PBMCs, the subject from whom the PBMCs are obtained may be given a pre-treatment with GCSF for mobilising mononuclear cell subpopulations. The PBMC composition may further be enriched for specific subsets of mononuclear cells as specified in further detail below.

In step (b) an expression construct comprising a nucleotide sequence encoding a polypeptide having IL-10 activity is introduced into at least part of the mononuclear cells in the composition. The nucleotide sequence encodes a polypeptide having IL-10 activity as defined above. The nucleotide sequence encoding a polypeptide having IL-10 activity may be homologous or heterologous to the species or to the subject from which the mononuclear cells are derived. Preferably, the nucleotide sequence encoding a polypeptide having IL-10 activity is homologous to the species or to the subject (e.g. a autologous allelic variant of the IL-10 amino acid sequence) into which the transgenic mononuclear cells are to be infused, so as to avoid imrnmunogenicity of the IL-10 polypeptide expressed from the transgene in the subject.

The expression construct can be any nucleic acid construct comprising a nucleotide sequence encoding a polypeptide having IL-10 activity that is suitable for introduction into the desired target cells, e.g. PBMCs, and that is capable of expressing the IL-10 polypeptide upon introduction into these cells. In the expression construct, the nucleotide sequence encoding the mature IL-10 polypeptide is preferably operably linked to expression signals, such as a signal sequence and transcription regulatory sequence including at least a promoter. The expression signals preferably allow expression of an IL-10 encoding nucleotide sequence in PBMCs. Thus, in the expression construct the nucleotide sequence encoding the mature IL-10 polypeptide is preferably operably linked to a nucleotide sequence encoding a signal sequence to direct secretion of the mature IL-10 from the cells expressing the construct. Preferably, the sequence encodes a signal sequence that is native to the sequence encoding the mature IL-10, e.g. the signal sequence consisting of amino acid 1-18 of SEQ ID NO. 1 or amino acids 1-23 of SEQ ID NO. 2. However, other suitable signal sequence that are capable of directing secretion of mature IL-10 from mononuclear cells may also be applied. In the expression construct the nucleotide sequence encoding a polypeptide having IL-10 activity preferably is operably linked to a promoter. The promoter is a promoter that is preferably active or can be induced to be active in PBMCs. The promoter may be a constitutive promoter, an inducible promoter or a tissue specific promoter, preferably specific for PBMCs or a subset of PBMCs. Suitable promoters for expression of the nucleotide sequence encoding an IL-10 polypeptide include e.g. cytomegalovirus (CMV) intermediate early promoter, viral long terminal repeat promoters (LTRs), such as those from murine moloney leukaemia virus MV) rous sarcoma virus, or HTLV-1, the simian virus 40 (SV 40) early promoter and the herpes simplex virus thymidine linase promoter and the human IL-2 promoter.[5] The expression construct may further comprise additional sequence elements for the expression of the nucleotide sequence encoding an IL-10 polypeptide, such as transcriptional enhancers and/or silencers, transcriptional terminators, and polyA-addition sites.

The expression construct may optionally comprise a second or one or more further nucleotide sequence coding for a second or further protein. The second or further protein may be a (selectable) marker protein that allows for the identification, selection and/or screening for PBMCs containing the expression construct. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual ($3^{rd}$ edition), Cold Spring Harbor Laboratory, Cold Spring Harbor Laboratory Press, New York.

Alternatively, the second or further nucleotide sequence may encode a protein that provides for fail-safe mechanism that allows to cure a subject from the IL-10 transgenic mononuclear cells of the invention, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see e.g. Clair et al., 1987, Antimicrob. Agents Chemother. 31: 844-849).

The nucleotide sequence coding for the marker protein is preferably also operably linked to a promoter for expression in PBMCs as described above for the nucleotide sequence encoding an IL-10 polypeptide.

The expression construct may be in the form of any nucleic acid capable of being introduced into PBMCs. The expression construct may be DNA, RNA or a combination of both; it may be a naked nucleic acid molecule, such as a plasmid or a linear DNA or RNA fragment; and it may be a single or a double stranded nucleic acid molecule. The expression construct may thus be a non-viral vector such as a plasmid or linear nucleic acid that may be packaged in e.g. a liposome for efficient delivery into the PBMCs. Alternatively, the expression construct is a viral vector that may be used to transduce or infect the PBMCs. The expression construct preferably is safe, efficient, and reliable and allows for expression, preferably controlled expression of the IL-10 transgene, and for some therapeutic purposes long term expression of the transgene is preferred. At present viral vectors are preferred because they are far more efficient agents for gene transfer as compared to the non-viral agents. Suitable viral expression constructs include e.g. vectors that are based on adenovirus, adeno-associated virus (AAV) or retroviruses as recently reviewed by[22-24].

Adenoviral and AAV vectors infect a wide number of dividing and non-dividing cell types. In addition adenoviral vectors are capable of high levels of transgene expression. However, because of the episomal nature of the adenoviral and AAV vectors after cell entry, these viral vectors are most suited for therapeutic applications requiring only transient expression of the transgene[25]. Preferred adenoviral vectors are modified to reduce the host response as reviewed by Russell[25].

Preferred viral vectors for use in the present invention are however retroviral vectors because they integrate efficiently into the genome of the target cell and they do not transfer any viral gene, thus alleviating the risk of immune response against the transgenic cells. Both of these properties are advantageous for achieving sustained expression of the transgene. A further advantage of the retroviral vectors is their large cloning capacity of up to 8 kb.

Two varieties of retroviral expression constructs may be used in the present invention: onco-retroviral based vectors such as e.g. vectors based on Moloney murine leukemia virus (MMLV) or lentiviral vectors such as e.g. vectors based on human immunodeficiency virus (HIV). A preferred oncoretroviral based expression construct is an MMLV expression construct. MMLV expression constructs are generated from plasmids that contain the gene(s) of interest (i.e. the nucleotide sequence encoding an IL-10 polypeptide and optionally a nucleotide sequence encoding a marker or other second protein, e.g. for regulation of expression of IL-10) flanked by the two MMLV LTR. Production of the MMLV expression construct requires the use of a packaging cell line to provide the viral proteins necessary for incorporation of the expression construct within viral particle that are capable to infect the PBMCs. The modified viral particles are replication-defective and retain only one round of infectivity, since they do contain any viral gene. Because retroviral vectors integrate in the host genome, the transgene is maintained after cell division. Combined with the efficient and sustained expression of the retroviral promoter present in the LTRs (the viral promoter), retroviral vectors may advantageously be used for long-term transgene expression. Methods for the construction and use of MMLV expression constructs are described by [22] and in U.S. Pat. Nos. 5,693,508, 5,817,491, 5,834,256, and 6,017,761.

Alternatively, lentiviral based expression constructs may be applied in the present invention. Lentiviral vectors have the unique ability to infect non-dividing cells[26]. Methods for the construction and use of lentiviral based expression constructs are described in U.S. Pat. Nos. 6,165,782, 6,207,455, 6,218,181, 6,277,633 and 6,323,031 and in [27] [28].

Retroviral expression constructs may be modified to alter the retroviral vector host range[29] [30]. The first step of wild-type retroviral infection is the recognition of a specific cell-surface receptor by the viral envelope, encoded by the env gene[31]. The host specificity of retroviruses is therefore primarily dictated by the nature of the envelope proteins that they carry. E.g., murine cells normally express mCAT-1 (cationic amino acid), which is recognised by the MMLV ecotropic envelope, and human cells express Ram-1 (phosphate transporter), the receptor for the MMLV 4070 amphotropic envelope. However, not all cell types, not even hematopoietic progenitor cells, are equally well infected with retroviruses. By means of genetic manipulation retroviral expression constructs may be modified to express different envelope proteins, a method known as "pseudotyping". For example, pseudotyping a retrovirus with the VSV-G envelope allows the entering of host cells via nonspecific binding to membrane phospholipids and permits the concentration of viral particles by ultracentrifugation.[32] Lentiviral vectors can be pseudotyped with the G protein from the vesicular stomatitis virus (VSV-G) to expand the host range beyond their natural 'target' cells, the CD4+ T cells.[33] In addition, MMLV vectors can be pseudotyped with truncated HIV glycoproteins to mediate specific gene transfer to CD4+ T cells.[34] Another strategy for altering gene delivery involves decorating the surface of viral particles with agents that display an affinity for cell-surface markers that are different from the natural receptor. A third strategy relies on the genetic modification of the retroviral envelope glycoprotein,[29] e.g. by using a packaging cell line based on Gibbon ape leukaemia virus (GALV).[35]

General recombinant DNA techniques for the construction of the expression constructs of the invention are described in Ausubel et al., "Current Protocols in Molecular Biology", Greene Publishing and Wiley-Interscience, New York (1987) and in Sambrook and Russel (2001, supra); both of which are incorporated herein by reference in their entirety.

The expression construct comprising the nucleotide sequence encoding an IL-10 polypeptide may be introduced into the PBMCs using a variety of methods available to the skilled person and depending on the nature of the expression construct. Non-viral expression constructs may be used to transform at least part of the PBMCs using e.g. biolistic transfection, electroporation, or lipofection (see Sambrook and Russel (2001) supra). The same methods may be applied to transfect the naked DNAs of viral expression constructs. However, preferably viral expression constructs are packaged into viral particles using the appropriate packaging cell lines and helper viruses and are then used to infect the PBMCs. Methods for packaging viral expression constructs and subsequent infection of PBMCs are described in the above listed references on the use of viral expression constructs.

Finally in step (c) the mononuclear cells overexpressing IL-10 are recovered. Recovery of the mononuclear cells overexpressing IL-10 at least means that the mononuclear cells subjected to step (b) are obtained for further use or storage. However, preferably recovery of the mononuclear cells overexpressing IL-10 subsequent to step (b) involves one or more of (a) washing of the cells; (b) changing the medium containing the cells; (c) further incubation of the cells to allow for expression of the IL-10 transgene; (d) enrichment for cells (over) expressing the IL-10 transgene, e.g. by selection, screening or sorting of cells expressing the transgene; (e) enrichment for specific subsets of the PBMCs (expressing the IL-10 transgene) as herein described below; and/or (f) formulation of the cells into pharmaceutical compositions for use in therapeutic and/or diagnostic methods as described below.

In a preferred method according to the invention, the composition comprising peripheral blood mononuclear cells is enriched for a subfraction of the peripheral blood mononuclear cells. Enrichment for a subfraction is herein understood to mean that in a preparation enriched for a given subfraction of PBMCs a higher percentage of cells belonging to that subfraction is present as compared to the non-enriched starting PBMC preparation. Preferably the percentage of the enriched cells is at least 1.1, 1.2, 1.5, 2.0, 5.0, 10, 100, 1000 or 10.000 times higher as compared to the non-enriched starting PBMC preparation. Specific subfractions for which the PBMCs may be enriched include e.g. lymphocytes, B cells, T cells, CD4+ cells, monocytes or dendritic cells (DC), MHC class II-positive or -negative cells, or combinations of these cells. Various methods are available in the art for the enrichment for specific subfractions present in the PBMC bulk. Specific subfractions of PBMCs may e.g. be enriched by red cell lysis, density centrifugation, by sorting on cell-sorter using fluorescent labelling of cell surface markers specific for a given subset of PBMCs, or by expanding specific subsets of PBMCs by incubation of the PBMCs under conditions that favour the proliferation and development of a given subset of PBMCs, e.g. using specific growth factors and/or interleukins (see e.g.[36]). A composition of PBMCs enriched for lymphocytes may be obtained by ficoll hypaque gradient density centrifugation, as described by[37]. A composition of PBMCs enriched for T cells may be obtained by immunomagnetic purification using antibodies to deplete all non-T cells and IgG-coated magnetic beads and a magnetic separation apparatus as described by[38]. A composition of PBMCs enriched for CD45RA+ T cells may be obtained as described by cliniMACS (antibiotin microbeads)(Miltenyi Biotec, Auburn, Calif., USA). A composition of PBMCs enriched for CD4+ T cells may be obtained by flow cytometry sorting using fluorescently labelled antibodies for CD4+ T cells, as described by[39]. A composition of PBMCs enriched for monocytes may be obtained by adherence, flow cytometry or Percoll density centrifugation, as described by[40]. A composition of PBMCs enriched for dendritic cells (DCs) may be obtained by culturing monocytes, isolated from PBMCs, with IL-4 and GM-CSF, as described by[41].

Thus, in a preferred method of the invention the PBMCs are allowed or induced to proliferate prior to step (b). The PBMCs are allowed to proliferate at least one cell cycle. Preferably the PBMCs are allowed or induced to proliferate in the presence of a proliferating agent. Preferred proliferating agents include e.g. anti-CD3/anti-CD28 antibodies, IL-2, PHA, ConA, GM-CSF and IL-4. In a further preferred method of the invention the mononuclear cells are enriched for a subfraction of mononuclear cells subsequent to step (b), i.e., subsequent to the introduction of the IL-10 transgene. Enrichment for specific subfractions of mononuclear cells may be performed as described above for the enrichment prior to step (b). In addition, the enrichment subsequent to step (b) may include the enrichment for cells (over)expressing the IL-10 transgene. Enrichment for cells (over)expressing the IL-10 transgene may be performed by direct sorting or screening for cells expressing IL-10, using e.g. labelled anti-IL-10 antibodies. However, most conveniently cells (over) expressing the IL-10 transgene are selected using an expression construct comprising a second nucleotide sequence coding for a marker protein as described above. Cells (over) expressing the IL-10 transgene may then be sorted using a fluorescently labelled marker protein such GFP or one of its variants or by using an antibody. Alternatively, cells (over) expressing the IL-10 transgene may be selected for by growth in a selective medium allowing only growth of cells expressing a selectable marker gene such as described above. Thus, in a preferred method of the invention the mononuclear cells are enriched subsequent to step (b) for cells (over)expressing the IL-10 transgene. Whether or not it is necessary to culture the PBMCs prior to step (b) depends on both the type of vector that is used for the introduction of the IL-10 transgene (e.g. MMLV- and Lenti viral-based vectors are capable of infection non-dividing cells whereas most other viral vectors are not), and on the type of mononuclear cell to be used (e.g. PBMCs may be enriched for dendritic cells (DCs) by culturing monocytes, isolated from PBMCs, with IL-4 and GM-CSF, as described above).

A particularly preferred method relates to the production of T cells that are transgenic for IL-10 and that functionally behave as regulatory T cells in that they express IL-10 and have anti-inflammatory and immunosuppressive functions. This method comprises the steps of: (a) optionally, culturing PBMCs in the presence of a proliferating agent such as phytohemagglutinin (PHA), or αCD3/CD28 and/or IL-2 (preculturing of the PBMCs is not necessary when MMLV or lenti viral vectors are used for the introduction of the IL-10 transgene in step (b)); (b) introducing an IL-10 expression construct as described above; (c) optionally, sorting the T cells or selecting cells expressing the IL-10 transgene; and (d) optionally, expanding the cells in the presence of a feeder mixture consisting of irradiated PBMCs, irradiated JY cells, anti-CD3/anti-CD28 antibodies, PHA and/or IL-2. The thus obtained transgenic regulatory T cells are characterised by their biological activity as evidenced by decreased proliferation of autologous responder cells and decreased production of the pro-inflammatory cytokine IL-12 by dendritic cells in co-culture experiments.

The mononuclear cells overexpressing IL-10 of the invention are further preferably characterised in that the cells are polyclonal and in that the cells are preferably not specific for a predetermined antigen.

In a further aspect the invention relates to compositions comprising the IL-10 overexpressing mononuclear cells of the invention. These compositions are obtained using any of the methods outlined above. Likewise the invention relates to compositions comprising IL-10 overexpressing T cells as describes herein, for use as a medicament. Preferably the medicament is used for treatment of any of the diseases mentioned herein. Preferably the composition is a pharmaceutical composition. The pharmaceutical composition of the invention comprises the IL-10 overexpressing mononuclear cells as obtained in the methods described above and a pharmaceutically acceptable carrier. The preferred form depends on the intended mode of administration and therapeutic application. The pharmaceutical carrier can be any compatible, non-toxic substance suitable to deliver the polypeptides to the patient. Sterile water, alcohol, fats, waxes, and inert solids may be used as the carrier. Pharmaceutically acceptable adjuvants, buffering agents, dispersing agents, and the like, may also be incorporated into the pharmaceutical compositions. The pharmaceutical composition comprising the IL-10 overexpressing mononuclear cells is preferably administered parentally. Preparations comprising the IL-10 overexpressing mononuclear cells for parental administration must be sterile. Sterilisation of component other than the cells is readily accomplished by filtration through sterile filtration membranes. The cells themselves are obtained, prepared and kept under sterile conditions, for which purpose antibiotics may be include in the culture media. The parental route for administration of the IL-10 overexpressing mononuclear cells is in accord with known methods, e.g. injection or infusion by intravenous, intraperitoneal, intracerebral, intramuscular, intraocular, intra-arterial, intradermal or intralesional routes. IL-10 overexpressing mononuclear cells are administered continuously by infusion or by bolus injection. A typical composition for intravenous infusion could be made up to contain 100 to 500 ml of sterile 0.9% NaCl or 5% glucose optionally supplemented with a 20% albumin solution and 100 to 500 mg of the C1 inhibitor. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

In another aspect the invention relates to a method for producing a pharmaceutical composition comprising IL-10 overexpressing mononuclear cells. The method comprises at least the steps of mixing the IL-10 overexpressing mononuclear cells obtained in the methods described above with a pharmaceutically acceptable carrier as described above.

In a further aspect the invention relates to methods of treating diseases associated with undesired activation and/or expansion of T cells such as autoimmune diseases, transplant rejection, graft-versus-host disease, inflammatory diseases, parasitic diseases and allergic diseases. Preferably the diseases that may be treated with the methods of the invention are Th1-mediated disease, more preferably Th1-mediated inflammatory diseases. Th1-mediated (inflammatory) diseases to be treated with the methods of the invention include e.g. chronic inflammatory diseases and disorders, such as Crohn's disease, rheumatoid arthritis, reactive arthritis, including Lyme disease, insulin-dependent diabetes, colitis, pancreatitis, inflammatory lung and eye diseases, organ-specific autoimmunity, including multiple sclerosis, Hashimoto's thyroiditis, Grave's disease and chronic articular reumatism, contact dermatitis, psoriasis, graft rejection, graft versus host disease, sarcoidosis. In addition other T cell mediated disorders may be treated with the methods of the invention, including e.g. atopic conditions, such as asthma and allergy, including allergic rhinitis, atopic dermatitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy. In accordance with the invention, the method of treatment comprises administering any of the pharmaceutical compositions comprising the IL-10 overexpressing mononuclear cells as defined above, to a subject suffering from any of the diseases associated with undesired activation and/or expansion of T cells as listed above.

In the methods of treatment of the invention, compositions comprising IL-10 overexpressing T cells, such as IL-10 overexpressing regulatory T cells are preferably used in the treatment of any of the above mentioned Th1-mediated (inflammatory) diseases. In these methods the amount of the composition that is administered to a subject suffering from a Th1-mediated (inflammatory) diseases preferably is sufficient to effect a modification of the natural course of the disease and/or in an amount that has a corticosteroid sparing effect. Compositions comprising IL-10 overexpressing T cells, such as IL-10 overexpressing regulatory T cells are preferably used in the treatment of Crohn's disease, whereby a subject suffering from Crohn's disease is administered an amount of the composition that is effective to prevent disease relapses. Compositions comprising IL-10 overexpressing T cells, such as IL-10 overexpressing regulatory T cells are preferably used in the treatment of arthritis, whereby a subject suffering from arthritis is administered an amount of the composition that is effective to prevent the formation of new erosions and/or to prevent surgery.

In the methods of treatment of the invention, compositions comprising IL-10 overexpressing regulatory dendritic cells are preferably used in the treatment of graft (transplant) rejection. Preferably, in this method a subject suffering from graft rejection is administered an amount of the composition has a sparing effect on the use of immunosuppressives.

In the methods of treatment of the invention, compositions comprising IL-10 overexpressing monocytes are preferably used in the treatment of acute overwhelming inflammatory conditions, such as systemic sepsis. Preferably, in this method a subject suffering from an acute overwhelming inflammatory condition is administered an amount of the composition that is effective in maintaining or restoring blood pressure to normal levels and/or that reduces end-organ damage and/or ischemia reperfusion.

Preferably, in any of the above methods the pharmaceutical composition comprising the IL-10 overexpressing mononuclear cells as defined above is administered via an intravenous, intra-arterial or intradermal route. In any of these methods, the pharmaceutical composition may be administered by (continuous) infusion or by bolus injection(s), or by combinations thereof. Preferably, in any of the above methods (the pharmaceutical compositions comprising) the IL-10 overexpressing mononuclear cells are administered in a therapeutically effective amount, preferably such that the stated therapeutic effects are achieved.

In a further aspect the invention relates to use of the IL-10 overexpressing mononuclear cells as defined above, in the manufacture of a medicament or a pharmaceutical composition for use in any therapeutic methods for treating the diseases associated with undesired activation and/or expansion of T cells as listed above. The medicament or pharmaceutical composition preferably is suitable for administration via an intravenous intra-arterial or intradermal route.

FACS analysis and sorting of CD4 and GFP expressing cells was performed 48 hours after transduction with the IL-10-GFP containing MMLV vector. The y-axis represents CD4 expression and the x-axis represents GFP fluorescence. Percentages of transduced $GFP^+CD4^+$ and non-transduced control $GFP^-CD4^+$ cells of gated viable lymphocytes are indicated before (left panel) and after sorting (right panels). This is a representative image of 11 independent transductions.

Figure 2:
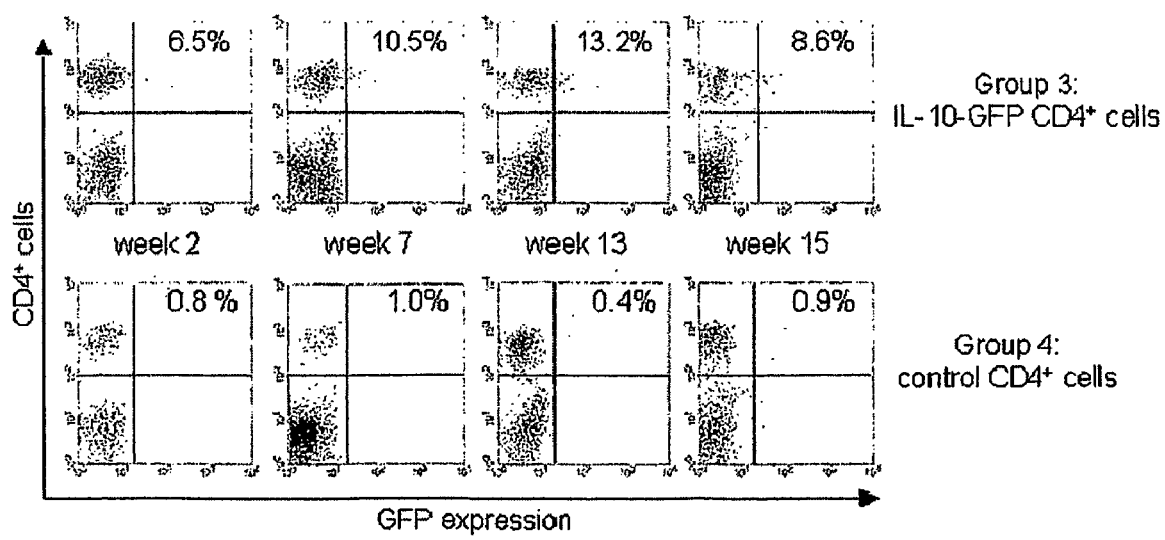

FIG. 2: Survival of GFP expressing cells in peripheral blood of SCID mice reconstituted with $CD_{45}RB^{high}$ $CD4^+$ cells FACS analysis of peripheral blood was performed at 2, 7, 13 and 15 weeks after transfer of IL-10-GFP $CD4^+$ (upper panel) or control $CD4^+$ cells (lower panel). The y-axis represents CD4 expression and the x-axis represents GFP fluorescence of gated viable lymphocytes. Representative images of 1 out of 12 mice are shown. Mean percentages of $GFP^+$ cells in the $CD4^+$ population are indicated.

Figure 3A:
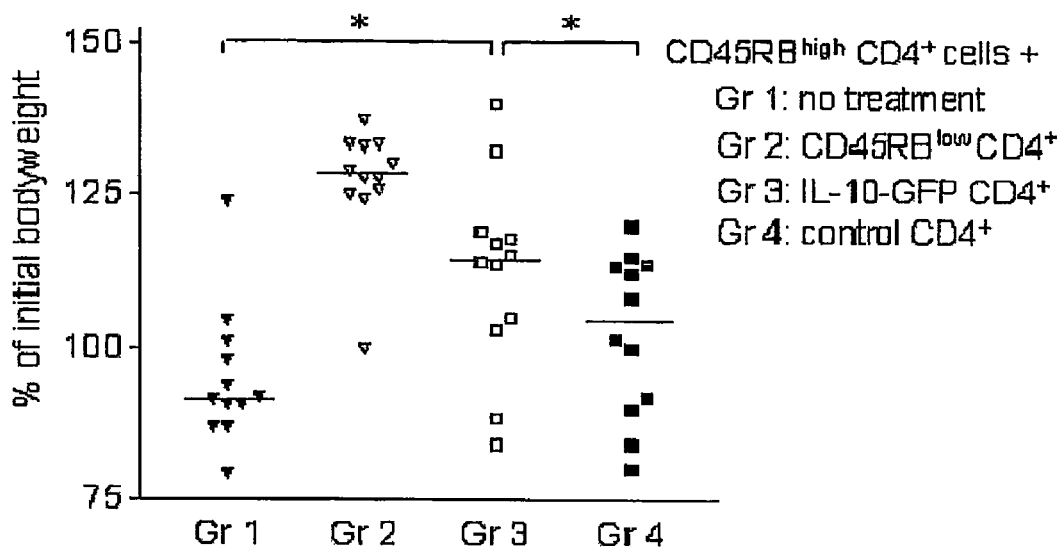
Figure 3B:
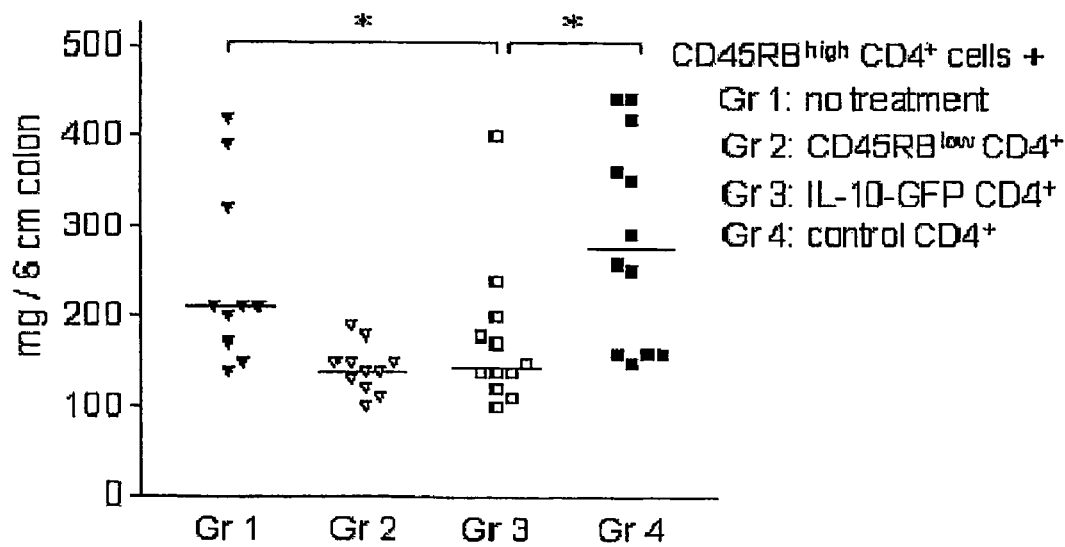

FIG. 3: IL-10 transduced $CD4^+$ cells reduce wasting and increase of colon weight SCID mice received $CD45RB^{high}$ $CD4^+$ cells alone or in combination with other subpopulations as indicated. A) Body weights, measured at the end of the experiments, are expressed as a percentage of initial body weight. IL-10-GFP $CD4^+$ treated mice had significantly higher body weights than untreated ($p=0.013$) or control $CD4^+$ T cell treated mice ($p=0.031$). Data are pooled from two separate experiments. B) The weight of the last 6 cm of the colon was determined upon sacrifice. IL-10-GFP $CD4^+$ treated mice had significantly lower colon weights than untreated ($p=0.034$) or control $CD4^+$ cell treated mice ($p=0.007$). Each symbol represents an individual mouse. Bar indicates median weight for each group. Data are pooled from two separate experiments.

Figure 4:
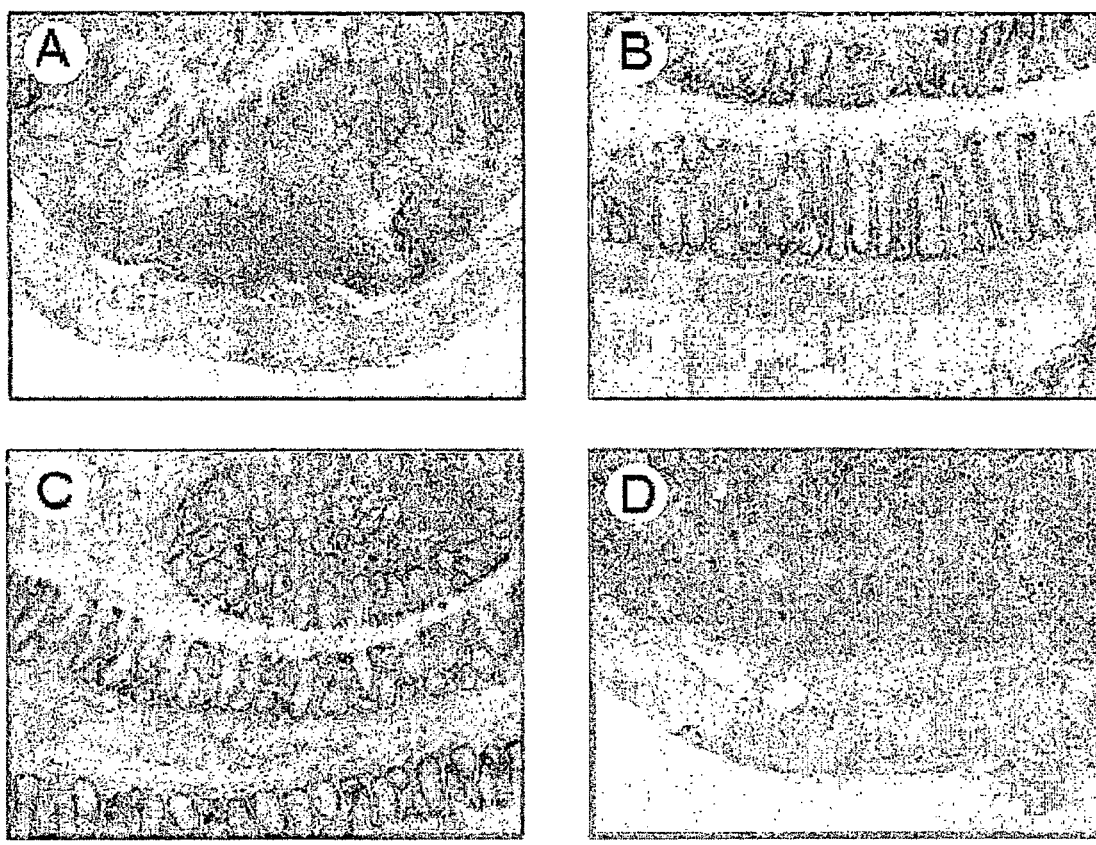

FIG. 4: Colon of SCID mice after transfer of $CD45RB^{high}$ $CD4^+$ cells alone or in combination with other subpopulations A) Severe colitis induced by $CD45RB^{high}$ $CD4^+$ cells, characterised by an extensive inflammatory cell infiltrate, epithelial cell hyperplasia, and loss of goblet cells. B) Colon of a mouse treated with $CD45RB^{low}$ $CD4^+$ cells. This picture shows normal colon architecture. C) Colon of a mouse treated with IL-10-GFP $CD4^+$ cells, showing a normal architecture with a small number of leukocytes in the mucosa and a large number of goblet cells in the crypts. D) Colitis in a mouse treated with control $CD4^+$ cells; histological features included crypt hyperplasia, ulceration and crypt abscesses. Hematoxylin and eosin staining. Original magnifications: 33×.

Figure 5:
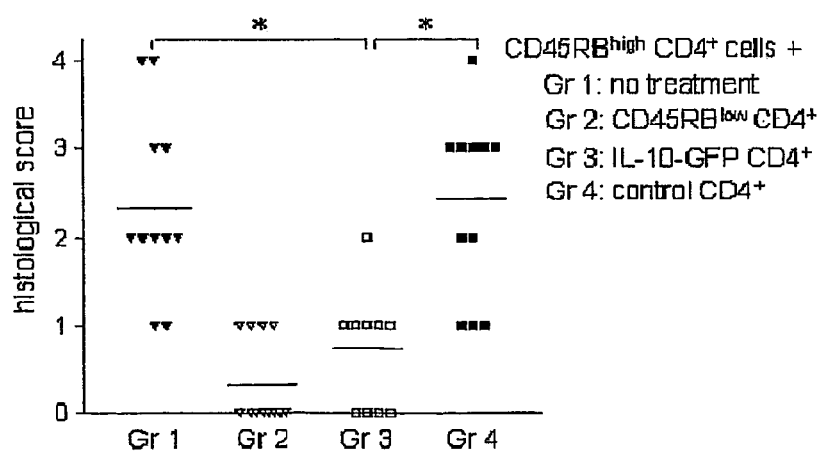

FIG. 5: Prevention of colitis in mice treated with IL-10-GFP $CD4^+$ cells

SCID mice received $CD45RB^{high}$ $CD4^+$ cells alone or in combination with other subpopulations as indicated. The extent of mucosal inflammation was examined and graded (see Materials and Methods). Each symbol represents an individual mouse. Bars indicate mean colitis score for each group and * indicates a significant difference between IL-10-GFP CD4+ cell treated mice and untreated ($p<0.001$) or control CD4+ cell treated mice ($p<0.001$).

Figure 6:
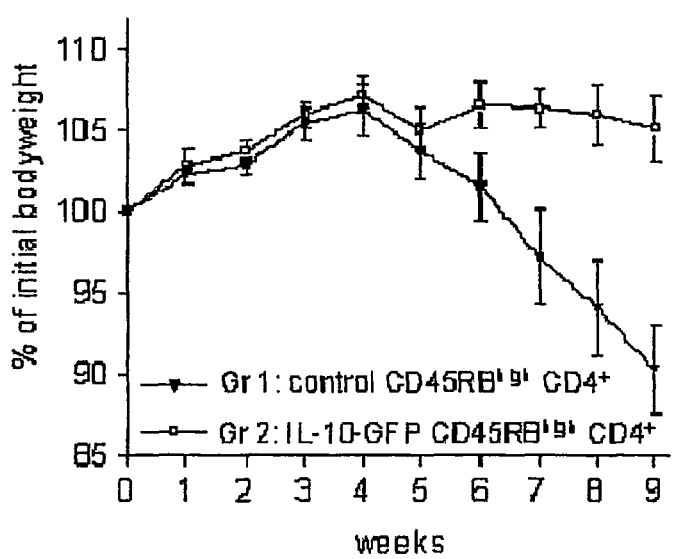

FIG. 6: IL-10-GFP transduced CD45RB$^{high}$ CD4+ cells prevent loss of body weight SCID mice received equal numbers of control or IL-10-GFP CD45RB$^{high}$ CD4+ cells as indicated. Body weights were recorded twice weekly during the entire experiment. The change of weight is expressed as the mean percentage of initial weight per group±SEM. ANOVA for repeated measures indicated that bodyweights of the two groups differed significantly in time ($p<0.001$). Data are pooled from three separate experiments.

FIG. 7: IL-10-GFP expression in SCID mice reconstituted with IL-10-GFP CD45RB$^{high}$ CD4+ cells A) FACS analysis of colon, caudal and mesenteric lymph node and spleen cell suspensions was performed at sacrifice 9-12 weeks after transfer of control CD45RB$^{high}$ CD4+ cells (Group 1: upper panel) or IL-10-GFP CD45RB$^{high}$ CD4+ cells (Group 2: lower panel). The y-axis represents CD4 expression and the x-axis represents GFP fluorescence of gated viable lymphocytes. Representative images of 1 out of 14 mice (Group 1) and 12 mice (Group 2) are shown. Mean percentages of GFP+ cells in the CD4+ population are indicated. B) The expression of the IL-10-GFP transgene was assessed by reverse transcription of total colonic RNA and PCR as described in Material and Methods. The upper panel shows a PCR of mice receiving IL-10-GFP CD4+ cells (1) or non-transduced control CD4+ cells (2) and PCR of a plasmid containing the construct IL-10-IRES-GFP (3). Reverse transcription reaction with mouse β-actin primers was performed parallel to a control of RNA quality (lower panel). The 879 bp and 628 bp bands are specific for the IL-10-GFP transgene and β-actin eDNAs respectively.

Figure 8:
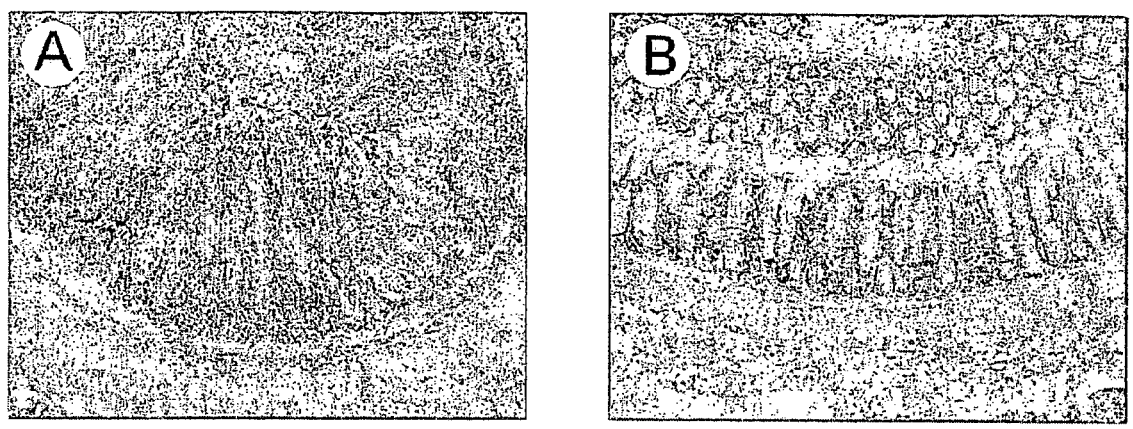

FIG. 8: Lack of intestinal inflammation in SCID recipients of IL-10-GFP CD45RB$^{high}$ CD4+ T cells Colon of SCID mice after transfer of control or IL-10-GFP CD45RB$^{high}$ CD4+ cells. A) Severe colitis induced by control CD45RB$^{high}$ CD4+ cells, characterised by a significant depletion of goblet cells and disorganisation of the epithelial cells (mean score 2.4±0.27) B) Some influx of mononuclear cells and granulocytes (mean score 1.0±0.21) ($p<0.001$). Hematoxylin and eosin staining. Original magnifications: 33×.

Figure 9:
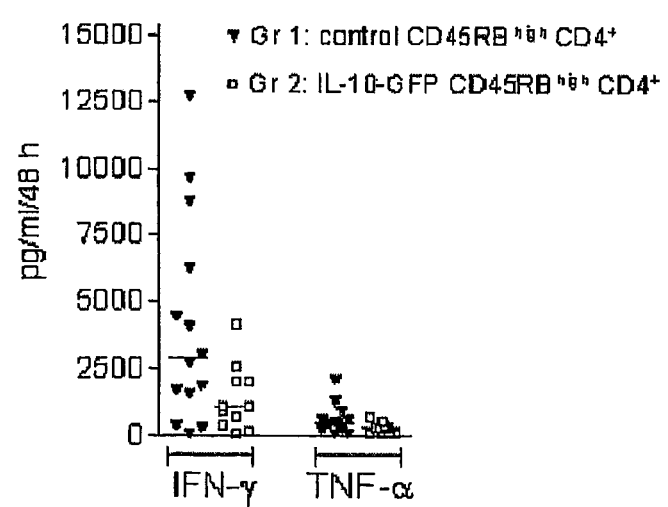

FIG. 9: Decreased production of IFN-γ by mesenteric lymph node cells after transfer of IL-10-GFP CD45RB$^{high}$ CD4+ cells Mesenteric lymph node cells were isolated 9-12 weeks after transfer of control CD45RB$^{high}$ CD4+ cells (Group 1) or IL-10-GFP CD45RB$^{high}$ CD4+ cells (Group 2). Cells ($1\times10^5$/well) were stimulated with αCD3/CD28 and IFN-γ and TNF-α production were measured after 48 hours in the supernatants. Mesenteric lymph node cells from IL-10-GFP CD45RB$^{high}$ CD4+ reconstituted mice produced less IFN-γ compared with the control mice ($p=0.05$). Each symbol represents an individual mouse. Data are pooled from three separate experiments.

Figure 10:
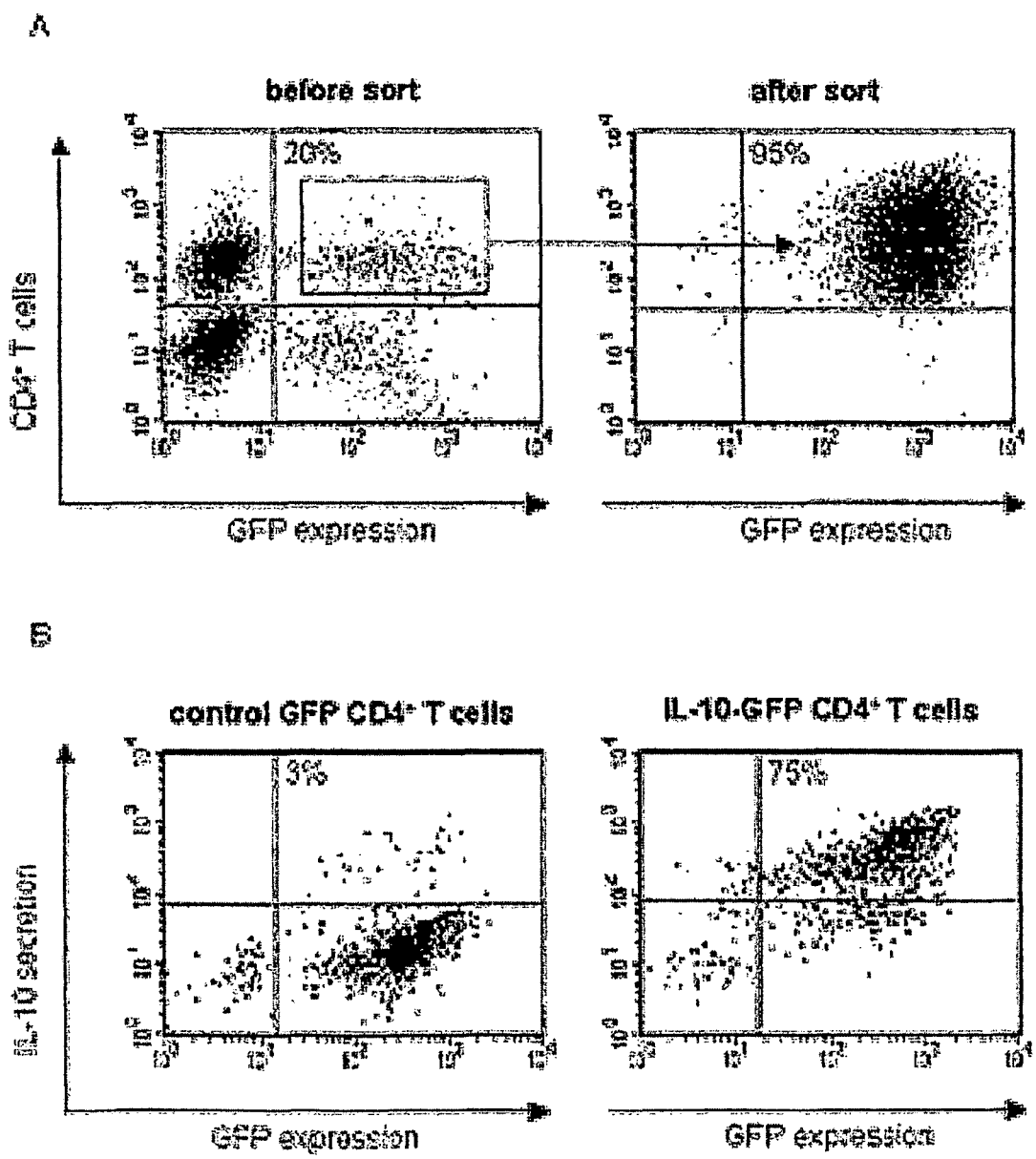

FIG. 10: FACS analysis and sorting of IL-10-GFP transduced CD4+. cells

A) FACS analysis and sorting of CD4 and GFP expressing cells was performed 48 hours after transduction with the IL-10-GFP containing MMLV vector. The y-axis represents CD4 expression and the x-axis represents GFP fluorescence. Percentages of GFP+ CD4+ cells are indicated before (left panel) and after sorting (right panel). This is a representative image of 8 independent transductions. B) An IL-10 secretion assay was performed with the sorted control GFP (left panel) and IL-10-GFP CD4+ cells (right panel) 1 month after the transduction as described in the materials and methods section. IL-10 secreting cells were stained with a PE labelled IL-10 detection antibody. The y-axis represents the IL-10 secretion and the x-axis represents the GFP fluorescence. Percentages of GFP+ IL-10+ cells are indicated for the control GFP (left panel) and IL-10-GFP CD4+ cells (right panel).

Figure 11A:
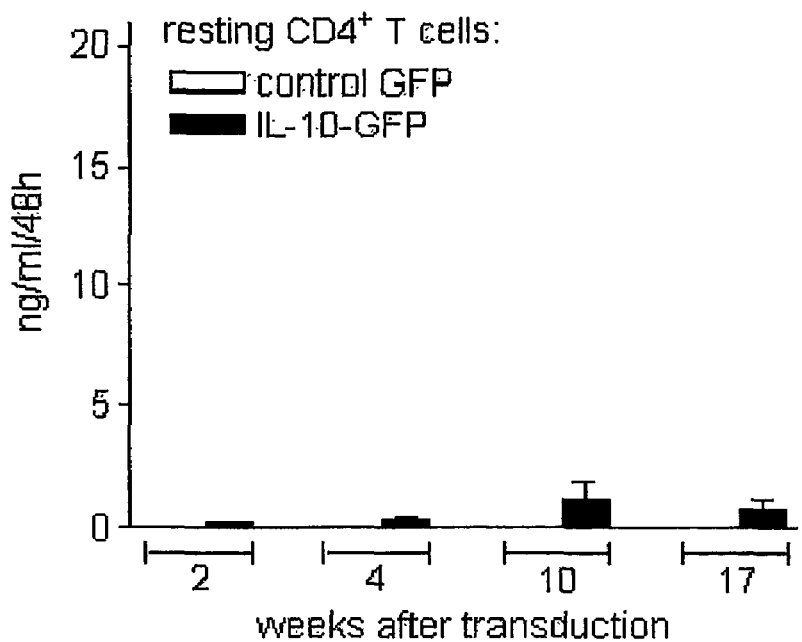
Figure 11B:
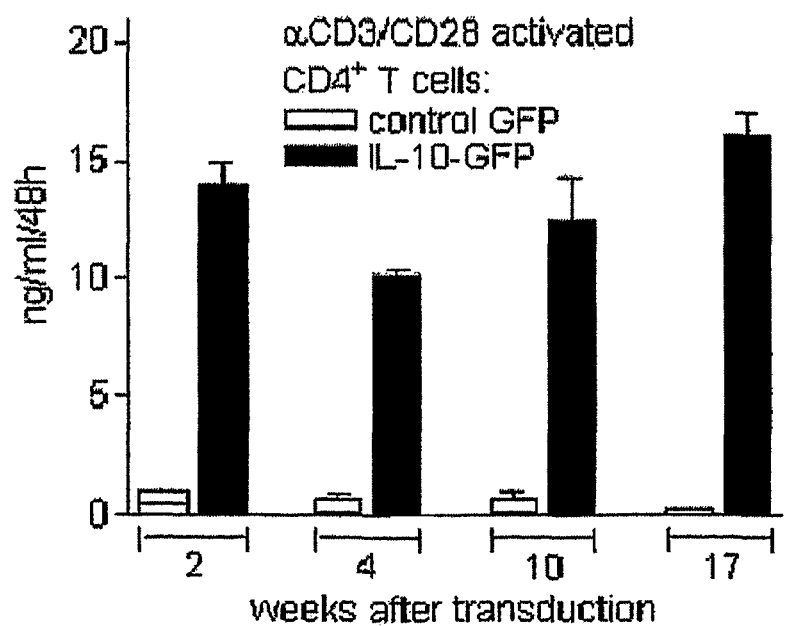

FIG. 11: IL-10 production by transduced CD4+ cells

CD4+ cells ($1\times10^5$/well) isolated from a healthy donor were cultured in the absence (A) or presence (B) of αCD3/CD28 mAbs for a period of 48 h on a 96 well plate as described in the materials and methods section. The supernatants were harvested and IL-10 concentrations were measured by ELISA at different time-points (2, 6, 10 and 17 weeks) after retroviral transduction. The production of IL-10 is expressed in nanograms of IL-10 per ml per 48 hours (ng/ml/48 h). Each value is the mean of duplicate measurements±SEM.

Figure 12:
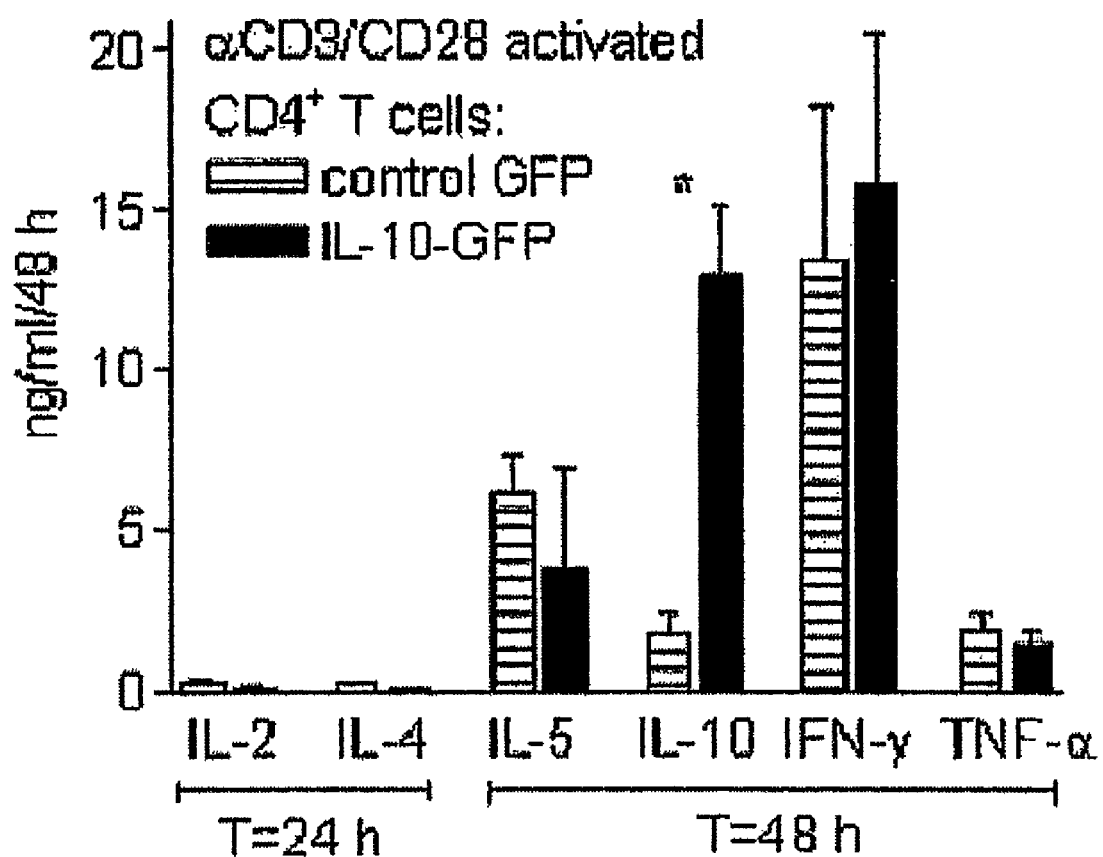

FIG. 12: Cytokine profile of transduced CD4+ cells

Cytokine concentrations were measured by ELISA in the supernatants of sorted GFP+CD4+ cells after transduction with either GFP or IL-10-GFP, as described in the legend of FIG. 2. IL-2 and IL-4 levels are given after 24 h of αCD3/CD28 stimulation, as these cytokines are rapidly consumed. The other cytokines are given after 48 h of stimulation, because their production peaked at this time point. Results of pooled data from 8 donors are expressed as mean±SEM and * represents a significant difference ($p=0.002$).

FIG. 13: Autocrine inhibition of IL-10-GFP transduced CD4+ cell proliferation A) The proliferation of transduced CD4+ cells from 2 donors was measured after a 48 hour incubation in the presence or absence of αCD3/CD28 mAbs. Incorporation of $^3$H-thymidine was determined after a pulse $^3$H-thymidine during the last 6 hours of culture. The proliferation rate is given as stimulation index, calculated as incorporated radioactivity of αCD3/CD28 activated CD4+ cells divided by the incorporated radioactivity of resting CD4+ cells. This experiment, performed in parallel with the cell cultures used for cytokine detection, represents one of 3 independent experiments yielding similar results. Each value is the mean of measurements±SEM and * indicates a significant difference ($p=0.004$).

B) Increasing numbers of irradiated or non-irradiated IL-10-GFP and control CD4+ cells ($0-5\times10^4$ cells/well) were stimulated for 3 days with allogeneic monocytes ($1\times10^4$/well). Incorporation of $^3$H-thymidine was determined after a pulse $^3$H-thymidine during the last 18 hours of culture. Each value is the mean of triplicate measurements±SEM and analysis of variance (ANOVA) for repeated measures indicated that proliferation of the two cell types differed significantly from $6.3\times10^3$ cells/well and onwards ($p<0.001$). The results are representative of 3 independent experiments.

FIG. 14: Inhibition of the proliferative response of autologous responder cells to alloantigens in the presence of IL-10, transduced cells or their supernatants Cultured CD4+ cells or freshly isolated PBMCs ($5\times10^4$/well) were stimulated for 3 days with allogeneic monocytes ($1\times10^4$/well). A) In the presence of increasing concentrations of rIL-10 (0 to 20 ng/ml). B) In the presence of supernatants of the transduced CD4+ cells ($1\times10^5$/well), harvested after 48 h αCD3/CD28 stimulation. C) In the presence of irradiated IL-10-GFP or control CD4+ cells ($2.5\times10^4$/well). Incorporation of $^3$H-thymidine was determined after a pulse $^3$H-thymidine during the last 18 hours of culture. Each value is the mean of triplicate measurements±SEM and * represents a significant difference (p<0.05). The results are representative of 3 independent experiments.

Figure 15:
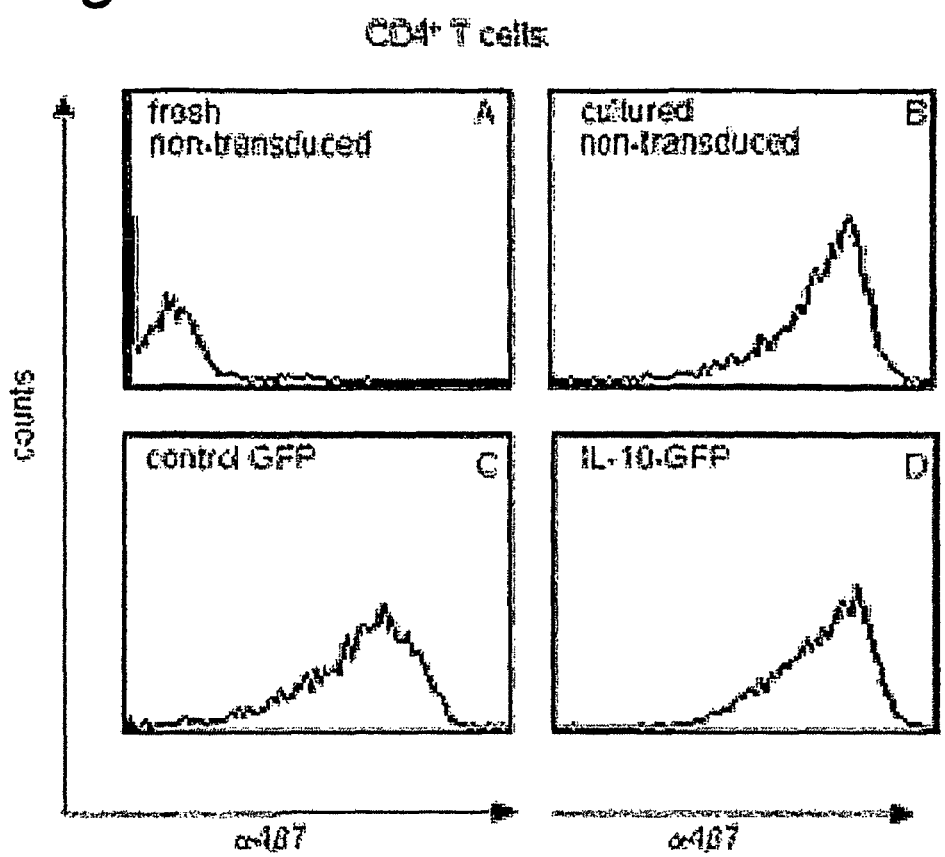

FIG. 15: High expression of α4β7 on fresh and cultured human CD4+ cells

Flow cytometry analysis of α4β7 expression on A) fresh CD4+ cells of a healthy donor, cultured CD4+ ells that were either B) non-transduced or C) transduced with the control GFP vector or d) the IL-10-GFP vector. The y-axis represents the relative cell number (counts) and the x-axis represents α4β7 expression. The results shown are representative for 8 donors.

Figure 16:
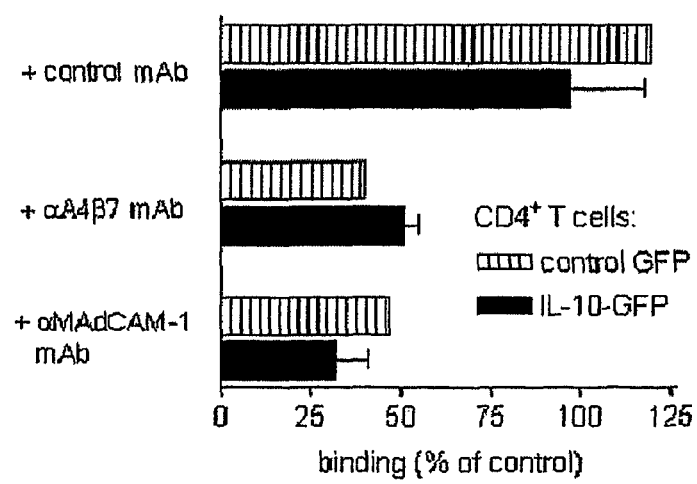

FIG. 16: Inhibition of CD4+ cell adhesion to MAdCAM-1 transfected 293T cells by αA4β7 and αMAdCAM-1 mAbs Adhesion of sorted CD4+ cells, transduced with GFP (1 donor) or IL-10-GFP (2 donors), to MAdCAM-1 transfected 293T cells was determined after preincubation with or without the following mAbs: 145 2C11 (control), act-1 (αA4β7) or MECA-367 (αMAdCAM-1). Fluorescent-labelled CD4+ cells were added to a 96 well plate that contained confluent MAdCAM-1 transfected 293T cells or control 293T cells. Relative binding inhibition was referred to the maximum binding achieved in the absence of mAbs (as described in Materials and Methods).

EXAMPLES

Example 1

Interleukin-10 Transduced T Lymphocytes Prevent Colitis in the SCID Mice Transfer Model 1.1 Materials and Methods
1.1.1 Mice BALB/c and C.B.-17 SCID mice were purchased from Charles River (Charles River, Someren, the Netherlands) and maintained in filter-top cages under specific-pathogen free conditions at our animal care facility. All experiments were approved by the animal welfare committee. Mice were used at 7-10 weeks of age.

1.1.2 Production of Replication-Defective Retrovirus

The LZRSpBMN-IRES-GFP retroviral plasmid (referred to as GFP) was constructed as described previously.[42] Briefly, GFP complementary DNA (cDNA) (Clontech, Palo Alto, Calif.) was cloned downstream of an internal ribosome entry site (IRES) in the LZRS retroviral vector (kindly provided by G. Nolan)[43] and expressed from the retroviral long terminal repeat of the Moloney murine leukemia virus (MMLV). A 536-bp PCR fragment containing the human IL-10 cDNA[44] was amplified from human cDNA with primers containing a BamHI (fw: GGATCCACCATGCACAGCTCAGCACT-GCTCTGT) and a Xho I (rv: CTCGAGTCAGTTTCG-TATCTTCATTGTCATGT) restriction site. The fragment was sequenced and cloned in the BamHI/XhoI sites upstream of the IRES in LZRSpBMN-IRES-GFP. The final bicistronic retroviral reporter construct was termed LZRSpBMN-IL-10-IRES-GFP and referred to as IL-10-GFP.

Transfection of an amphotropic producer cell line was performed as described previously.[45] Viral supernatants were used to infect the ecotropic 293T Phoenix packaging cells (kindly provided by G. Nolan) for 16 h in the presence of 10 µg/ml DEAE (Sigma, St Louis, Mich.). Single infected Phoenix cells were sorted by a FACS Vantage Cell Sorter (Becton Dickinson, Mountain View, Calif.) using an automatic cell deposition unit (Becton Dickinson), and then used to generate virus-containing supernatants with titres ranging from $10^5$-$10^6$ IU/ml.

1.1.3 Infection/Transduction of Splenocytes

BALB/c splenocytes were isolated using filter cell strainers (Becton Dickinson) and red cells were lysed. Splenocytes ($3-5\times10^6$/well) were seeded in 24 well plates (Costar Europe Ltd, Badhoevedorp, The Netherlands) in Iscoves modified Dulbecco's medium (Biowhittaker) supplemented with 10% FCS (Biowhittaker), 50 µM 2-ME (Merck, Darmstadt, Germany), 1% penicillin-streptomycin-glutamine solution (GibcoBRL, Grand Island, N.Y.) and 20 U/ml of recombinant human IL-2 (Chiron, Amsterdam, The Netherlands). Cells were activated for 24 h with immobilised anti-(α)CD3 (1:30 concentration, clone 145-2C11) and soluble αCD28 monoclonal antibodies (mAb) (1:1000 concentration, Pharmingen, San Diego, Calif.) under standard conditions (37° C., 5% $CO_2$). Retrovirus-containing supernatants were added for overnight (O/N) incubation. Medium was exchanged with supplemented Iscove's medium and αCD28 mAb (1:3000 concentration, Pharmingen) for an additional 48 hours. Splenocytes were harvested and stained with cychrome-conjugated αCD4 mAb (Coulter-Immunotech, Marseille, France) to analyse the transduction efficiency. The cells were either used directly for injection into BALB/c mice or, in separate experiments, sorted into subsets of CD4 and GFP expressing cells using a FACS Vantage Cell Sorter (Becton Dickinson). Sorted subsets were reanalysed following the initial collection to confirm fraction purity which was routinely >90%. In a second set of experiments, splenocytes were also stained using phycoerythrin (PE)-conjugated CD45RB (Coulter-Immunotech) and sorted into subsets of $CD45RB^{high}$ CD4 and GFP expressing cells. Upon reanalysis, the sorted cells were >90% pure. A small fraction of the sorted cells ($1\times10^5$) was used for analysis of cytokine production and the remaining cells were injected intraperitoneally in recipient mice (see below).

1.1.4 Induction of $CD45RB^{high}$ Transfer Colitis and Treatment Protocol

Chronic $CD45RB^{high}$ transfer colitis was induced as previously described.[46] Briefly, BALB/c splenocytes were first enriched for CD4+ cells by red cell lysis and negative selection using the following rat anti-mouse mabs: B220 (clone RA3-6B2), Mac-1 (clone M1/70), and CD8α (clone 53-6.7) (gift from Dr. R. Mebius, Vrije Universiteit Medical Center, Amsterdam, The Netherlands). MAb-stained cells were removed in a magnetic field using sheep anti rat IgG coated magnetic beads (Dynal, Hamburg, Germany). The resulting CD4 enriched cells were stained with cychrome (Cy)-conjugated CD4 and fluorescein isothiocyanate (FITC)-conjugated CD45RB (both Pharmingen) mAbs. Subpopulations of CD4 cells were generated by two color sorting on the FACS sorter (Becton Dickinson). Populations were >95% pure upon reanalysis.

C.B-17 SCID mice received intraperitoneal injections of sorted CD4+ cell subpopulations in PBS. To induce colitis, $CD45RB^{high}$ CD4+ cells ($1-4\times10^5$) were transferred to 4 groups of mice in a first set of experiments. The mice received $CD45RB^{high}$ CD4+ cells alone (Group 1) or in combination with $CD45RB^{low}$ cells (Group 2), sorted IL-10-GFP CD4+ cells (Group 3) or control CD4+ cells (Group 4). In a second set of experiments, SCID mice received either non-transduced control $CD_{45}RB^{high}$ CD4+ cells or IL-10-GFP transduced $CD45RB^{high}$ CD4+ cells.

1.1.5 Assessment of Inflammation

Mice were weighed twice a week and wasting disease was determined by percentage of weight loss from baseline body weight. Peripheral blood was drawn at different time points by retro-orbital sinus puncture for plasma IL-10 measurement and FACS scan analysis of GFP expression. At necropsy, colons were removed through a midline incision and opened longitudinally. The wet weight of the distal 6 cm was recorded and used as an index of disease-related intestinal wall thickening. Subsequently, the colons were longitudinally divided in two parts; one for histology, the other for cytokine assay, RNA isolation, or detection of GFP expressing cells.

Intestinal cells were isolated using an automated mechanical disaggregating device (Medimachine System, Dako, Denmark). Cells were filtered through a cell strainer (Becton Dickinson) and resuspended in FACS buffer (0.5% BSA, 0.01% $NaN_3$ and 0.3 mM EDTA in PBS, pH 7.4). Colon homogenates were made with a tissue homogeniser in 9 volumes of Greenberger lysis buffer (300 mM NaCl, 15 mM Tris, 2 mM $MgCl_2$, 2 mM Triton (X-100), Pepstatin A, Leupeptin, Aprotoninie (all 20 ng/ml), Ph 7.4). Tissue was lysed for 30 minutes on ice followed by two times centrifugation 910 min., 14000 g). Homogenates were stored at −20° C. until further use.

Cell suspensions of the spleens and caudal and mesenteric lymph nodes were prepared by filtration through a cell strainer (Becton Dickinson) and red cell lysis of splenocyte suspensions. If cell numbers were sufficient, cells were washed in supplemented RPMI medium (Biowhittaker) and plated ($1 \times 10^5$ cells/well) on 96-well round bottom plates (Costar) in a final volume of 200 µl in the presence of αCD3/CD28 mAbs for assessment of cytokine production. The remaining cells were resuspended in FACS buffer for detection of GFP expression. Culture supernatants were collected from 4 wells after 48 hours, pooled and stored at −20° C. until use.

1.1.6 Cytokine Analysis

Cytokine concentrations (IL-2, IL-4, IL-5, TNF-α and IFN-γ in cell culture supernatants derived from spleen and lymph nodes were measured by a cytometric bead assay (CBA, Becton Dickinson) according to manufacturer's instructions. Briefly, a mixture of cytokine capture beads, which have discrete fluorescence intensity characteristics, was added to the supernatants and cytokine standards. Next, samples were incubated at RT with a Th1/Th2 PE-conjugated detection reagent, containing α-murine IL-2, IL-4, IL-5, TNF-α and IFN-γ Abs. After 2 h, samples were washed in wash buffer and analysed on a FACS Calibur using CBA software (Becton Dickinson). Expression of human IL-10 was analysed in plasma samples, spleen and caudal and mesenteric lymph node culture supernatants, and colon homogenates ELISA (CLB, Amsterdam, The Netherlands). A TNF-α ELISA was performed on the colon homogenates (R&D Systems, Abingdon, UK).

1.1.7 Analysis of GFP Expression

Cells from peripheral blood, colon, spleen and lymph nodes were incubated for 20 min on ice with fluorochrome-conjugated CD4-Cy, CD45RB-PE, CD69-PE or isotype controls (all Pharmingen) and analysed using a FACS Calibur (Becton Dickinson) in conjunction with FACScan software (Becton Dickinson). Gates were set to exclusively detect viable lymphocytes and negative green fluorescence was set at less than 1%, using cells from a mouse that received control $CD4^+$ cells.

1.1.8 Histology

The longitudinally divided colons were rolled up and fixed in 4% formaline. Fixed tissues were embedded in paraffin, and 6 µm sections were stained with haematoxylin and eosin for histological grading. Inflammation in the transfer model was scored by an experienced pathologist blinded to treatment allocation on a scale of 0-4, representing no change to severe changes, as described previously.[46] The same pathologist scored the following parameters in the TNBS colitis model: 1) percentage of colon involved, 2) fibrosis, 3) oedema, 4) erosions and ulcerations, 5) crypt loss, 6) infiltration of mononuclear cells or 7) polymorphonuclear cells as described previously.[47] The total score ranges from 0 to a maximum of 20 points.

1.1.9 RT-PCR for IL-10-GFP

Total RNA was isolated from colon homogenates using TRIZOL (Gibco BRL) and treated with RNAase-free DNAase (GibcoBRL). First strand cDNA synthesis was carry out with 2-5 µg total RNA, 0.5 mM dNTPs, 250 ng random primers, 10 µM DTT, 40 U Ribonuclease inhibitor and 200 U of Moloney murine leukemia virus reverse transcriptase (MLV-RT) in a final volume of 20 µl, with buffer and incubations according to the instructions of GibcoBRL. Separate reaction tubes without reverse transcriptase were used as control of DNA contamination. PCR was performed in a thermocycler Gene AMP® PCR System 9700 (Perkin Elmer, Norwalk, Conn., USA) using 2-4 µl of cDNA template, 0.2 mM dNTPs, 0.2 µM of each primer (IL-10fw5'CTAACGTTCTGGCCGAAGC3'; GFPrv5'TCTTGTAGTTGCCGTCGTCC3') and 1 U of AmpliTaq polymerase (Perkin Elmer Corp., Branchburg, N.J., USA), in 25 µl final volume containing 10 mM Tris-HCl pH 9.0, 1.5 mM $MgCl_2$, 50 mM KCl and 0.1% Triton X-100. The cycling conditions were as follows: denaturation 94 C for 4 min., then 30 cycles of (94 C, 30 sec; 50 C 30 sec; 72 C 45 sec) and a final extension at 72 C for 5 min. A second PCR using β-actin primers (mβ-actinfw 5'GTCAGAAGGACTC-CTATGTG3'; mβ-actinrv 5'GCT CGTTGCCAATAGT-GATG3') was performed under the same conditions. The PCR products were separated on a 1% agarose gel and visualised by UV illumination.

1.1.10 Statistical Analysis

Differences between treatment groups were analysed by the Mann-Whitney U test. Differences between treatment groups in time were tested by analysis of variance (ANOVA) for repeated measures. Results are expressed as median (range) or as mean±SEM where appropriate. All statistical tests were done using SPSS for Windows (Microsoft Corporation, Redmind, Wash., USA). A two-tailed p value <0.05 was considered to represent a significant difference.

1.2. Results 1.2.1 Efficient Transduction and Sorting of Murine Splenocytes

Figure 1:
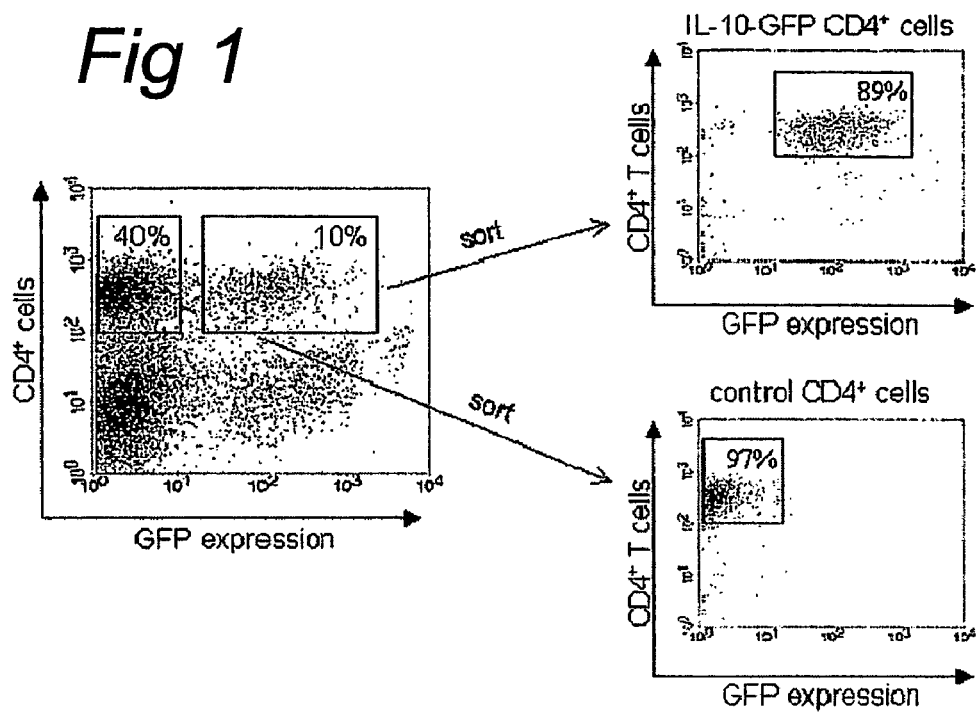
FIG. 1: Efficient transduction and sorting of murine splenocytes

To generate IL-10 expressing $CD4^+$ cells, activated murine splenocytes were transduced with the IL-10-GFP retroviral construct. αCD3/CD28 mAb-activated splenocytes routinely consisted of 42±5% $CD4^+$ cells. The percentage of GFP-expressing cells (transduction efficiency) in several independent experiments (n=11) was 16±2%. After 48 hours, viable $GFP^+CD4^+$-expressing splenocytes were sorted using a FACS Vantage flow cytometer (FIG. 1), while $GFP^-CD4^+$ cells served as negative controls, resulting in populations of 89±2% ($GFP^+CD4^+$ cells) and 97±1% ($GFP^-CD4^+$ cells), respectively.

As previously reported[45, 48, 49], production of transgene by transduced cells correlates well to expression of the marker gene GFP using a bicistronic vector containing an IRES. The culture supernatants from activated and resting IL-10-GFP $CD4^+$ cells ($1 \times 10^6$/ml) contained up to 5700 and 178 pg IL-10/ml/48 h, respectively. In contrast, the supernatants of non-transduced cells did not contain detectable levels of IL-10. As we previously observed in human $CD4^+$ cells[45], the transduction procedure did not significantly alter/affect CD45RB expression (memory marker) or cytokine production (IL-2, IL-4, IL-5, IFN-γ and TNFα) in the absence or presence of αCD3/CD28 activation (Data not shown).

1.2.2 Long-Term Survival of IL-10-GFP Cells

Colitis was induced in SCID mice by the transfer of $CD45RB^{high}$ $CD4^+$ cells. SCID mice received $CD45RB^{high}$ $CD4^+$ cells alone (Group 1) or in combination with a single administration of $CD45RB^{low}$ $CD4^+$ cells (Group 2), IL-10-GFP $CD4^+$ cells (Group 3) or control non-transduced $CD4^+$ cells (Group 4) (see Table 1).

To study the survival of IL-10-GFP $CD4^+$ cells, we analysed the GFP expression of peripheral blood cells in the recipient mice by FACS at different times after transfer of IL-10-GFP $CD4^+$ cells. As shown in FIG. 2, $GFP^+$ $CD4^+$ cells were detected at all time points tested (2, 7, 13 and 15 weeks) in all mice (n=12), and after 15 weeks constituted a substantial proportion (8.6±1.0%) of the $CD4^+$ population. Virtually no autofluorescent cells were detected following transfer of control $CD4^+$ cells (0.9±0.3%, n=12).

In all mice tested (n=6 from each group) circulating levels of IL-10 were below the detection limit 2 weeks after transfer and upon sacrifice. Transfer of IL-10-GFP $CD4^+$ cells resulted in $GFP^+$ expressing cells in the spleen (11.2±0.7% of $CD4^+$ cells) and caudal lymph node (10.4±1.2% of $CD4^+$ cells), which drains the large intestine. Less than 1% $CD4^+$ cells displayed autofluorescence in the same organs after transfer of control $CD4^+$ cells. Hence, the IL-10-GFP transduced $CD4^+$ cells persisted in vivo and were effectively recruited into the large intestinal immune compartment.

TABLE 1

Experimental set-up transfer IL-10 $CD4^+$ cells

| | Cells injected | Number of cells (number of mice) | |
|---|---|---|---|
| Group | Phenotype | exp 1 | exp 2 |
| Group 1 | $CD45RB^{high}$ $CD4^+$ cells alone | $1.2 \times 10^5$ (n = 7) | $4.0 \times 10^5$ (n = 4)/ $2.7 \times 10^5$ (n = 3) |
| | $CD45RB^{high}$ $CD4^+$ cells | $1.2 \times 10^5$ (n = 18) | $4.0 \times 10^5$ (n = 10)/ $2.7 \times 10^5$ (n = 8) |
| Group 2 | +$CD45RB^{Low}$ $CD4^+$ cells | $0.6 \times 10^5$ (n = 6) | $2.6 \times 10^5$ (n = 3/3) |
| Group 3 | +IL-10-GFP $CD4^+$ cells | $2.6 \times 10^5$ (n = 6) | $3.4 \times 10^5$ (n = 4/2) |
| Group 4 | +control $CD4^+$ cells | $2.6 \times 10^5$ (n = 6) | $3.4 \times 10^5$ (n = 3/3) |

1.2.3 IL-10 Transduced $CD4^+$ Cells Prevent Transfer Colitis

To determine whether the IL-10-GFP $CD4^+$ cells were able to prevent colitis induced by transfer of $CD_{45}RB^{high}$ $CD4^+$ cells to SCID mice, we performed the experiments summarized in Table 1. In these experiments, the interval between transfer of $CD_{45}RB^{high}$ cells and cotransfer of IL-10-GFP transduced cells ranged from 4 to 14 days. The outcome of these experiments was identical, and therefore the data were pooled.

At 15-18 weeks after transfer, when mice transferred with $CD_{45}RB^{high}$ $CD4^+$ cells alone (Group 1) or cotransferred with control $CD4^+$ cells (Group 4) developed a hunched appearance and wasting disease (FIG. 3A), the experiment was terminated and all mice were sacrificed. As previously described[50], transfer of $CD45RB^{high}$ $CD4^+$ cells into SCID mice resulted in severe colitis, with an increase in colon weight (FIG. 3B) and histological signs of mucosal inflammation (FIGS. 4 and 5).

Mice that were cotreated with $CD45RB^{low}$ $CD4^+$ cells (Group 2), which are known to have a protective effect in this model, did not develop colitis as reflected by normal body weight gain/increase and normal colon weights (FIG. 3).

Treatment with IL-10-GFP $CD4^+$ cells (Group 3) also protected mice from induction of colitis: At the end of the experiment body weights were significantly higher compared to untreated (p=0.013) or control $CD4^+$ cell treated mice (p=0.031), and colon weights were significantly lower compared to untreated (p=0.034) or control $CD4^+$ cell treated mice (p=0.007). In contrast, cotransfer of the non-transduced control $CD4^+$ cells (Group 4) did not protect from colitis, and even seemed to exacerbate disease (FIG. 3). Representative histological sections from colons of the recipient SCID mice and total histological scores are shown in FIGS. 4 and 5, respectively. Colitis in mice that received $CD45RB^{high}$ $CD4^+$ cells (FIG. 4A) was characterised by an extensive inflammatory cell infiltrate, marked epithelial cell hyperplasia, and loss of goblet cells. The large intestine of mice in which $CD45RB^{low}$ $CD4^+$ cells were co-transferred (FIG. 4B) had no or minimal changes that consisted of influx of leukocytes and slight epithelial hyperplasia. Similarly, in IL-10-GFP $CD4^+$ cell recipients (FIG. 4C) either no or minimal histological changes were found, such as slight epithelial cell hyperplasia and some influx of leukocytes in the mucosa. By comparison, significant signs of colitis were detected in the recipients of control $CD4^+$ cells (FIG. 4D), and crypt abscesses and ulcerations were most severe in this group.

The total histological scores for all groups are shown in FIG. 5. Colonic inflammation was significantly reduced after transfer of IL-10-GFP $CD4^+$ cells compared to untreated (p=0.0004) or control $CD4^+$ cell treated mice (p=0.0007).

We next examined the cytokine production of lymphocytes isolated from the caudal lymph nodes and spleens of mice treated with the IL-10-GFP or the control CD4 cells. Cells ($1 \times 10^5$/well) were stimulated with αCD3/CD28 mAb in vitro, and IL-2, IL-4, IL-5, IFN-γ and TNFα levels in culture supernatants were measured using a CBA. Production of these cytokines by splenocytes was not altered by treatment with IL-10-GFP $CD4^+$ cells (Data not shown). In contrast, production of IFN-γ and TNF-α by caudal lymph node cells was lower in the IL-10-GFP $CD4^+$ cell treated mice (n=7 tested) (TNF-α 253 (40-1165) and IFN-γ 814 (40-6279) pg/ml/48 h) than in the control $CD4^+$ cell treated mice (n=5) (TNF-α: 924 (120-5000) and IFN-γ 3675 (240-13925) pg/ml/48 h), although this did not reach statistical significance. TNF-α and IL-10 levels in colon homogenates were measured by ELISA. IL-10-GFP $CD4^+$ cell treatment diminished TNF-α levels (n=6 tested) compared to control $CD4^+$ cell treatment (n=6 tested) (101 (46-135) vs. 253 (53-397) pg/ml, not significant). IL-10 levels were below the detection limit (<2.4 pg/ml) in the colon homogenates. However, IL-10 was detected in 4 out of 8 caudal lymph node and 7 out of 12 spleen cell supernatants of mice treated with IL-10-GFP $CD4^+$ cells. In contrast, IL-10 levels were below the detection limit in all caudal lymph node (n=5) and spleen cell (n=11) supernatants of mice treated with control $CD4^+$ cells.

These results suggest that the transfer of IL-10 producing $CD4^+$ cells preferentially inhibited inflammation in the local mucosal compartment, without interfering with systemic (spleen) immune activation.

1.2.4 IL-10 Transduced $CD45RB^{high}$ $CD4^+$ T Cells are Non-Pathogenic in SCID Mice It has been previously reported that transfer of $CD45RB^{high}$ $CD4^+$ cells isolated from IL-10 transgenic mice does not cause colitis in SCID mice.[5] We therefore performed a second set of experiments, in which $CD_{45}RB^{high}$ $CD4^+$ cells were sorted into IL-10-GFP transduced and non-transduced subsets in order to test for their ability to induce colitis after transfer into SCID mice (Table 2). Recipients of non-transduced control $CD45RB^{high}$ $CD4^+$ cells (Group 1) followed a typical course of disease, losing weight within about 4 weeks after cell transfer and remaining sick for the duration of the study (FIG. 6). In contrast, the recipients of IL-10-GFP CD45RB$^{high}$ CD4$^+$ cells (Group 2) gained weight early on and were able to maintain their weight during the entire experiment (ANOVA repeated measure test p<0.001 Group 1 versus Group 2:).

TABLE 2

Experimental set-up transfer IL-10 CD45RB$^{high}$ cells

| Cells injected | | Number of cells (number of mice) | | |
|---|---|---|---|---|
| Group | Phenotype | exp 3 | exp 4 | exp 5 |
| Group 1 | CD45RB$^{high}$ CD4$^+$ cells. | 2 × 10$^5$ (n = 7) | 2 × 10$^5$ (n = 4) | 2 × 10$^5$ (n = 3) |
| Group 2 | IL-10-GFP CD45RB$^{high}$ CD4$^+$ cell | 2 × 10$^5$ (n = 5) | 2 × 10$^5$ (n = 4) | 2 × 10$^5$ (n = 3) |

Figure 7A:
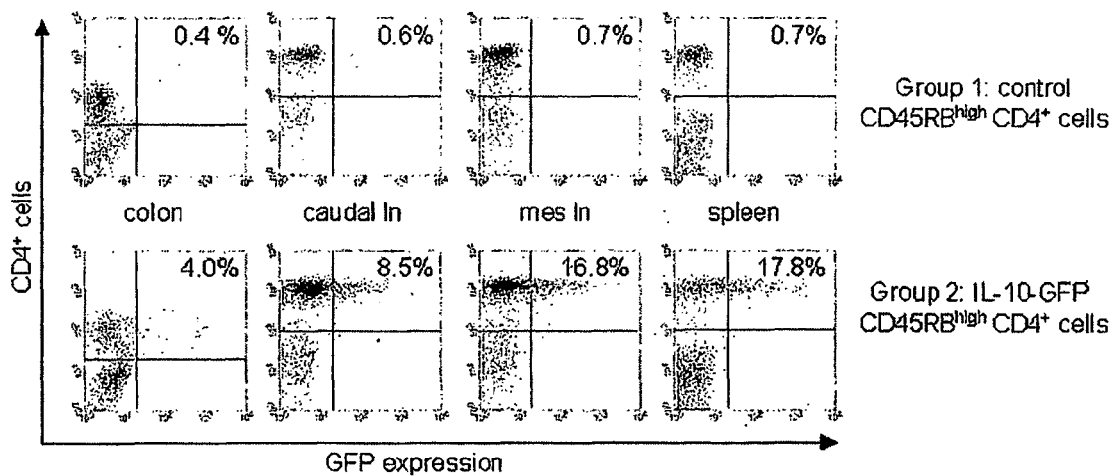
Figure 7B:
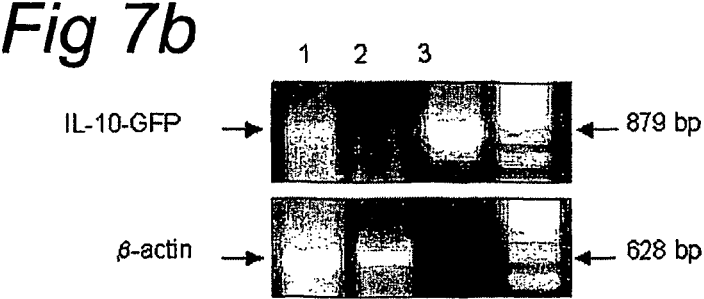

It is known that transfer of CD4$^+$ cells into SCID mice results in preferential repopulation of gut associated lymphoid tissues with immunocompetent CD4$^+$ T cells and subsequent expansion in the lamina propria of the host.[51,52] FACS analysis of intestinal lymphocytes revealed that GFP fluorescent CD4$^+$ cells were indeed present 12 weeks after transfer of IL-10-GFP CD45RB$^{high}$ CD4$^+$ cells (FIG. 7A). In addition, GFP fluorescent cells were found in the spleen, and the caudal and mesenteric lymph nodes (FIG. 7A). Using RT-PCR, the IL-10-GFP encoding mRNA was detected in colons from mice that were treated with IL-10-GFP CD4$^+$ cells 15 weeks after cell transfer, but not in the control treated mice (FIG. 7B).

As expected, recipients of control cells (n=14) had increased colon weights, whereas colon weights of IL-10-GFP CD45RB$^{high}$ CD4$^+$ cell recipients (n=12) were virtually normal (346±35 and 224±18 mg respectively, p=0.006). Histological analysis indicated that the colons of control CD45RB$^{high}$ CD4$^+$ cell recipients had the typical hallmarks of inflammation in this model (FIG. 8A). In contrast, only a minor influx of mononuclear cells and granulocytes in the colon was found after transfer of IL-10-GFP CD45RB$^{high}$ CD4$^+$ cells (FIG. 8B).

Cytokine levels (IL-2, IL-4, IL-5, IFN-γ and TNF-α levels in spleen cell supernatants were not different in the 2 groups (Data not shown). However, IFN-☐☐ production by mesenteric lymph node cells was lower after transfer of IL-10-GFP CD45RB$^{high}$ CD4$^+$ cells (FIG. 9, p=0.05), indicating that these cells modulated cytokine production in the lymph nodes that drain the intestine. In addition, TNF-γ concentrations in colon homogenates were lower in IL-10-GFP CD4$^+$ cell recipients than in control CD45RBhigh recipients (300 (260-441) versus 570 (472-669) pg/ml, p=0.05). IL-10 could be detected in 4 out of 5 colon homogenates of the IL-10-GFP CD$_{45}$RB$^{high}$ CD4$^+$ cell treated mice but not in homogenates of control mice. In addition, IL-10 was detected in 2 out of 9 mesenteric lymph node and 6 out of 9 spleen cell supernatants of the mice transferred with IL-10-GFP CD45RB$^{high}$ CD4$^+$ cells but not in control mice. Taken together, these results demonstrate that transduction of CD45RB$^{high}$ CD4$^+$ cells with the IL-10-GFP construct prevented induction of colitis in SCID mice. Moreover, the transduced cells migrated to the intestine and the draining lymph nodes and influenced local production of pro-inflammatory cytokines.

Additional experiments showed that transfer of bulk lymphocytes isolated from the spleens of wild-type mice resulted in survival of the GFP$^+$ cells in both IL-10$^{-/-}$ B1/6 mice and wild-type BALB/c for at least 2 to 6 weeks.

Example 2

Retroviral Transduction of Human T Cells 2.1 Methods and Materials
2.1.1 Vectors and Viral Production
Vectors and viral production were as described in Example 1.1.1
2.1.2 Retroviral Transduction of Human T Cells
PBMCs were obtained from healthy adults after informed consent by Ficoll HyPaque (Pharmacia, Uppsala, Sweden) density gradient centrifugation. PBMCs (1×10$^6$/well) were seeded in 24 well plates (Costar Europe Ltd, Badhoevedorp, The Netherlands) and cultured under standard conditions in Iscoves modified Dulbecco's medium (IMDM, Biowhittaker) supplemented with 10% human serum (Biowhittaker), 2 mM glutamine, and 1% antibiotic-antimycotic solution (GibcoBRL). Cells were stimulated with 1 μg/ml of phytohemagglutinin (PHA, Murex Diagnostics, Dartford, UK) and 10 U/ml of recombinant human IL-2 (Chiron, Amsterdam, The Netherlands) under standard conditions. After 48 hours, 5×10$^6$ cells were seeded in 6 well RetroNectin-coated plates (Retronectin; Takara, Otsu, Japan), and transduced overnight with 1 ml of retroviral supernatant, then, cells were washed and transferred to 24 well plates in supplemented IMDM. After at least 2 days the transduced cells were analysed by flow cytometry for GFP expression. T cells (3×10$^5$/well) were expanded in the presence of a feeder mixture consisting of irradiated allogeneic human PBMCs of two donors (1×10$^6$/ml each), 1×10$^5$/ml of irradiated JY cells, 100 ng/ml PHA and 10 U/ml IL-2.

2.1.3 Purification of Retrovirally Transduced CD4$^+$ T Cells
To obtain a purified CD4$^+$ T cell subset, eight to ten days after transduction, cells were stained with CD4-PE (Coulter-Immunotech, Marseille, France) and sorted in a FACS Vantage Cell Sorter (Becton Dickinson, Calif., USA) into subsets of positive and negative CD4$^+$ and GFP expressing cells. After sorting, a double-positive population was purified to at least 90%. The sorted CD4$^+$ GFP$^+$ T cells were expanded and cultured in the feeder mixture for further analysis.

2.1.4 Cytokine and Cell Proliferation Assays
The cytokine profile of transduced CD4$^+$ cells was determined 10 days after the addition of a feedermix. Cells were washed in medium and 1×10$^5$ cells/well were plated out on 96-well round bottom plates (Costar) in a final volume of 200 μl of medium in the absence or presence of immunobilised anti-(α)CD3 (clone SPV-T3b)[53] and 2 μg/ml soluble αCD28 monoclonal antibodies (mAb) (clone CLB-CD28/1 ascites fluid, CLB, Amsterdam, The Netherlands). After a 24 and 48-hour incubation, cell-free supernatants collected from 4 wells were pooled and stored at −20° C. until further use. Cytokine levels in culture supernatants were measured in duplicate by a sandwich enzyme-linked immunosorbent assays (ELISA) for IL-2 (R&D systems, Abingdon, UK), IL-4, IL-10, IFN-γ and TNF-α (CLB) and IL-5 (Pharmingen, San Diego, Calif., USA), according to manufacturer's instructions.

An IL-10 secretion assay (Miltenyi Biotec, Auburn, Calif., USA) was performed according to the instructions of the manufacturer, after 1-month culture. In short, transduced CD4$^+$ cells were stimulated for 24 h with αCD3/CD28 as described above. Subsequently, cells were harvested, washed and an IL-10 specific catch reagent (Miltenyi Biotec) was added and incubated for 5 min on ice. After a 45 min secretion period at 37° C., cells were washed and stained with a PE labelled IL-10 detection antibody (Miltenyi Biotec) and Cy5-CD4 (Beckman-Coulter, Fullerton, Calif., USA) for FACSscan (Becton Dickinson) analysis.

The proliferation rate of the transduced CD4$^+$ T cells was measured at the same time point (48 h) and under equal conditions (+/− activation) as cytokine production. During the last 6 hours of culture, cells were incubated with 0.25 µCi/well $^3$H-thymidine (Amersham, Les Ulis, France). At 48 hours the cells were lysed, the homogenates were harvested on a filter and the incorporated radioactivity was measured on a Topcount scintillation counter (Packard Instruments, Meriden, Conn., USA). The proliferation rate is given as stimulation index, calculated as incorporated radioactivity of αCD3/CD28 activated CD4$^+$ cells divided by the incorporated radioactivity of resting CD4$^+$ cells. In separate experiments, the proliferation rate of increasing numbers (up to $5 \times 10^4$/well) of sorted transduced CD4$^+$ cells was measured after stimulation with allogeneic monocytes ($1 \times 10^4$/well). Monocytes were isolated using Percoll (Pharmacia, Uppsala, Sweden) density centrifugation (90% CD14$^+$). Cells were cocultured in a final volume of 200 µl of medium in 96-well round bottom plates (Costar).

In coculture experiments, autologous responder cells (cultured CD4$^+$ cells and fresh PBMCs) ($5 \times 10^4$/well) were isolated as described above and stimulated with monocytes ($1 \times 10^4$/well). Cell proliferation assays were conducted in the presence of increasing concentrations of rIL-10 (0 to 20 ng/ml, Strathmann Biotec, Hannover, Germany) or supernatants of transduced cells ($1 \times 10^5$/well), collected after 48 h of αCD3/CD28 stimulation. Transduced CD4$^+$ cells were tested for their ability to suppress the proliferation of autologous CD4$^+$ cells and PBMCs. For suppression, increasing numbers (up to $5 \times 10^4$/well) of irradiated IL-10-GFP or control transduced CD4$^+$ cells were added. Cells were cocultured in a final volume of 200 µl of medium in 96-well round bottom plates (Costar). After 3 days, wells were pulsed for 16 hours with 0.25 µCi/well $^3$H-thymidine (Amersham) and the incorporated radioactivity was determined as described.

2.1.5 Analysis of IL-12 Production by Dendritic Cells

DCs were generated from PBMCs as described previously.[54, 55] In brief, monocytes isolated by Percoll density gradient centrifugation were cultured ($0.5 \times 10^6$/well) in IM supplemented with 1% FCS (Hyclone, Logan, Utah) and GM-CSF (500 U/ml, Schering-Plough, Uden, The Netherlands) and IL-4 (250 U/ml, PBH, Hannover, Germany). After 6 days of culture, irradiated IL-10-GFP or control transduced CD4$^+$ cells ($0.5 \times 10^6$ cells/well) were added in duplicate wells in the presence of GM-CSF (1000 U/ml). On day 8 DCs were harvested, washed extensively and plated ($2 \times 10^4$/well) in duplicate with CD40L expressing cells ($2 \times 10^4$/well, CD40L transfected J558L cell line kindly provided by Peter Lane, University of Birmingham, Birmingham, UK) in 96-well plates (Costar) in IMDM containing 10% FCS (Hyclone). DCs were cultured in the presence or absence of IFN-γ (1000 U/ml) in a final volume of 200 µl for 24 h. IL-12p70 levels were analysed in culture supernatants in duplicate by ELISA (R&D systems, Abingdon, UK), according to manufacturer's instructions.

2.1.6. Cell Surface Phenotyping

The expression of several activation and differentiation markers was studied on resting CD4$^+$ cells after transduction. Cells were harvested, washed with cold FACS buffer (0.5% BSA, 0.01% NaN$_3$ and 0.3 mM EDTA in PBS, pH 7.4) and incubated for 20 min on ice with the following mAbs: Cy5-CD4 (Beckman-Coulter), PE-CD154 (Immunotech, Hamburg, Germany), or unlabeled CD18, CD25, CD27, CD28 (all CLB), CD44 (Pharmingen), CD45RO (Dako, Glostrup, Denmark), CD62L (Becton Dickinson), CD152 (Immunotech), α4β7 (gift from Leukosite, Cambridge, Mass., USA), CXCR3 (Pharmingen), Q5/13 (NMC cl II, gift from S. Feronne, Medical College, Valhalla, N.Y., USA) followed by PE-rabbit-anti-mouse F(ab)$_2$ (Dako). Isotype controls included PE- and Cy5-conjugated IgG (Immunotech). Stained cells were analysed using a FACScan (Becton Dickinson) and the data were processed with CellQuest computer software.

2.1.7. Adhesion Assay

We investigated whether transduced CD4$^+$ cells were able to bind to the mucosal addressin MAdCAM-1 measuring their adhesion to 293T cells stably expressing the murine MAdCAM cDNA (kindly provided by Dr. S. Fong, Genentech Inc., San Francisco, Calif., USA). Transduced CD4$^+$ cells were labelled with 50 µM carboxyfluorescein diacetate succinimidyl ester (CFDSE: Molecular probes, Eugene, Oreg., USA) at 37° C. for 10 min, washed in ice-cold PBS and resuspended in adhesion assay medium consisting of Dulbecco's without phenol red (GibcoBRL) supplemented with 10% FCS (Biowhittaker), 2 mM glutamine, and 1% antibiotic-antimycotic solution (GibcoBRL). The CFDSE-labelled CD4$^+$ cells were preincubated with the following mAbs for 20 min before the adhesion assay: α4β7 (Act-1, gift from Leukosite), MAdCAM-1 (MECA-367, gift from Dr. R. Mebius, Free University, Amsterdam, The Netherlands) and a control antibody (145 2C11, gift from Dr. R. Mebius). MAdCAM-1 overexpressing and control 293T cells ($5 \times 10^4$/well) were plated on 96 well plates (Costar) and cultured for 24 hours. Labelled CD4$^+$ cells ($1 \times 10^5$/well) were added in quintuplicate and incubated for 30 min at 37° C. Non-adherent CD4$^+$ cells were washed with adhesion assay medium. Fluorescence was measured in a Cytofluor plate reader (Perceptive Biosystems, Framingham, Mass., USA) before and after washing. The adherence was calculated as the percentage of fluorescent cells remaining after washing. The maximum binding was calculated as the difference in adherence to MAdCAM-1 transfected and control 293T cells.

2.1.8. Statistics

Differences in cytokine production and proliferation between different cell populations were analysed by the non-parametric Mann-Whitney U test. Differences in proliferation were also tested by analysis of variance (ANOVA) for repeated measures. Results are expressed as the mean±SEM. A two-tailed p value of less than 0.05 was considered to represent a significant difference.

2.2 Results 2.2.1 Efficient Transduction and Stable Expression of GFP and IL-10 by Transduced CD4$^+$ T Cells Fresh PBMCs were stimulated with PHA and IL-2 for 48 hours. Stimulated PBMC populations routinely consisted of >90% CD3$^+$ cells (data not shown). The PBMCs were subsequently transduced with IL-10-GFP or GFP retroviral constructs and the transduction efficiencies were determined after 48 hours on the basis of GFP expression in viable cells. Transduction efficiencies ranged from 13 to 48%, with a mean of 26±3% (16 transductions performed in 8 different donors). PBMCs were sorted on the basis of CD4 and GFP expression using a FACS Vantage flow cytometer (FIG. 10A). GFP expression correlated well with IL-10 secretion as shown in FIG. 10B. Upon reanalysis, the sorted GFP$^+$ CD4$^+$ cells had a purity of 93±2%. This percentage remained constant during the entire period of cell culture (more than 4 months), indicating that the transgene was stably integrated and expressed. This is in agreement with a previous study describing stable transgene expression in human T cells for up to 6 months using the same LZRS vector containing telomerase.[56]

2.2.2 Cytokine Analysis

We first quantified the amount of IL-10 in the supernatants of sorted GFP+ CD4+ cell cultures from one healthy donor. The production of IL-10 by IL-10-GFP CD4+ cells was measured 2, 6, 10 and 17 weeks after transduction. It is clear from FIG. 11A that αCD3/CD28 activated IL-10-GFP CD4+ cells had a high and stable IL-10 production compared to control GFP CD4+ cells.

As previously reported, transgene expression increases substantially when retroviral transduced lymphocytes are reactivated by CD3/CD28 engagement.[57] IL-10-GFP CD4+ cells up-regulated IL-10 expression indeed after αCD3/CD28 stimulation significantly compared to resting cells. A representative example is given in FIGS. 11A and 11B. These results were highly reproducible when studied in 8 other donors: stimulated IL-10 production was 12.9±2.1 (FIG. 12) versus 0.59±0.06 ng/ml/48 h by resting IL-10-GFP CD4+ cells (p=0.003). αCD3/CD28 stimulation of control GFP CD4+ cells also led to a higher IL-10 expression (FIG. 12) compared to non-stimulated CD4+ cells (2.08±0.61 versus 0.19±0.1 ng/ml/48 h, P=0.002), though these levels were evidently lower than the IL-10 levels in the supernatants of the IL-10-GFP CD4+ cells.

To examine whether the cytokine profile was affected by transduction with IL-10-GFP, we measured the production of Th1 (IL-2, IFN-γ and TNF-α) and Th2 cytokines (IL-4, IL-5 and IL-10) after αCD3/CD28 stimulation (FIG. 12). IL-2 and IL-4 levels are provided after 24 h of stimulation, as they are rapidly consumed. The levels of the other cytokines are shown after 48 h stimulation, because their production peaked at this time point. IL-10-GFP CD4+ cells produced approximately 6-fold higher levels of IL-10 than control GFP CD4+ cells (p=0.002), but there was no significant difference in the production of Th1 and Th2 cytokines (FIG. 12). Remarkably, activation of both cell types resulted in high levels of IFN-γ.

Figure 13A:
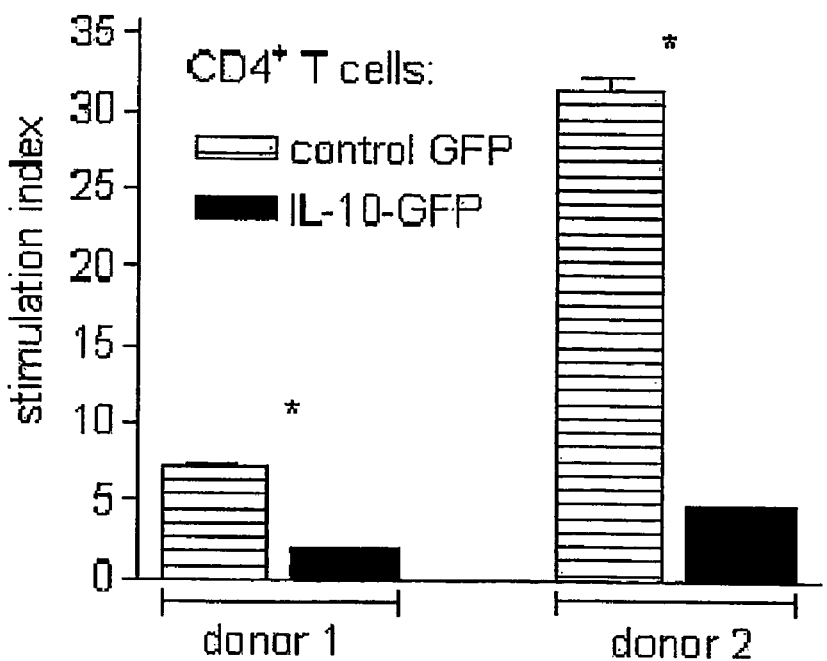
Figure 13B:
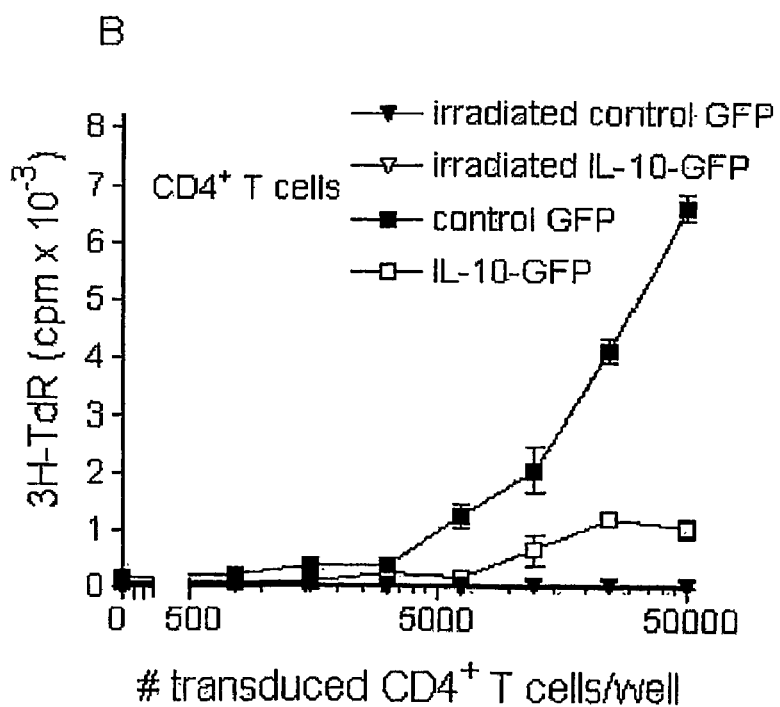

2.2.3 Increased IL-10 Production Leads to a Blunted Proliferative Response in IL-10-GFP Transduced CD4+ T Cells An important feature of IL-10 is the inhibition of T cell proliferation.[58, 59] To test this biological activity, we performed a $^3$H-thymidine incorporation assay on our transduced cell cultures in parallel to the cytokine secretion assays after 48 hours of αCD3/CD28 activation. FIG. 13A shows the stimulation index of 2 representative donors of a total of 6. The IL-10-GFP CD4+ cells had a reduced proliferative response to αCD3/CD28 activation in comparison to control GFP CD4+ cells. Similar results were obtained after 72 hours of αCD3/CD28 activation (Data not shown). These data indicate that the increased production of IL-10 by activated IL-10-GFP CD4+ cells, as shown in FIG. 12, reflects an increased IL-10 production per cell, as it could not be ascribed to an increased number of cells due to proliferation. In addition, IL-10-GFP CD4+ cells had a blunted proliferative response when stimulated with allogeneic monocytes in sharp contrast to the control GFP CD4+ cells (FIG. 13B).

Figure 14A:
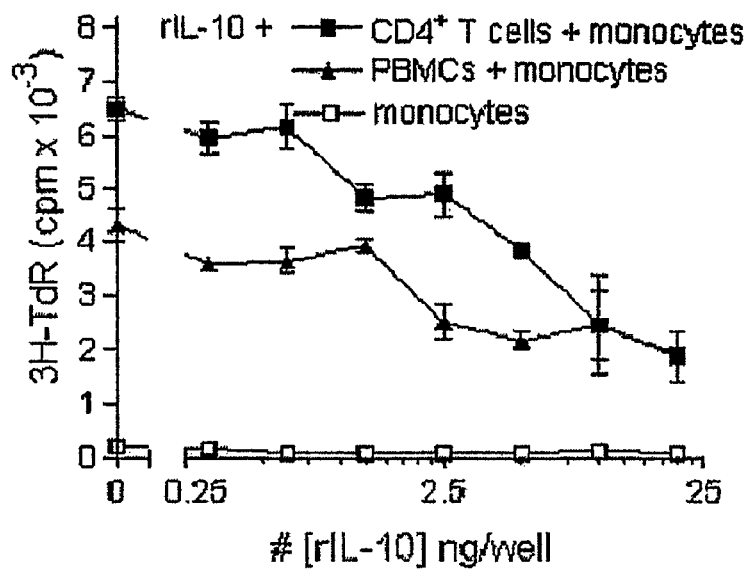
Figure 14B:
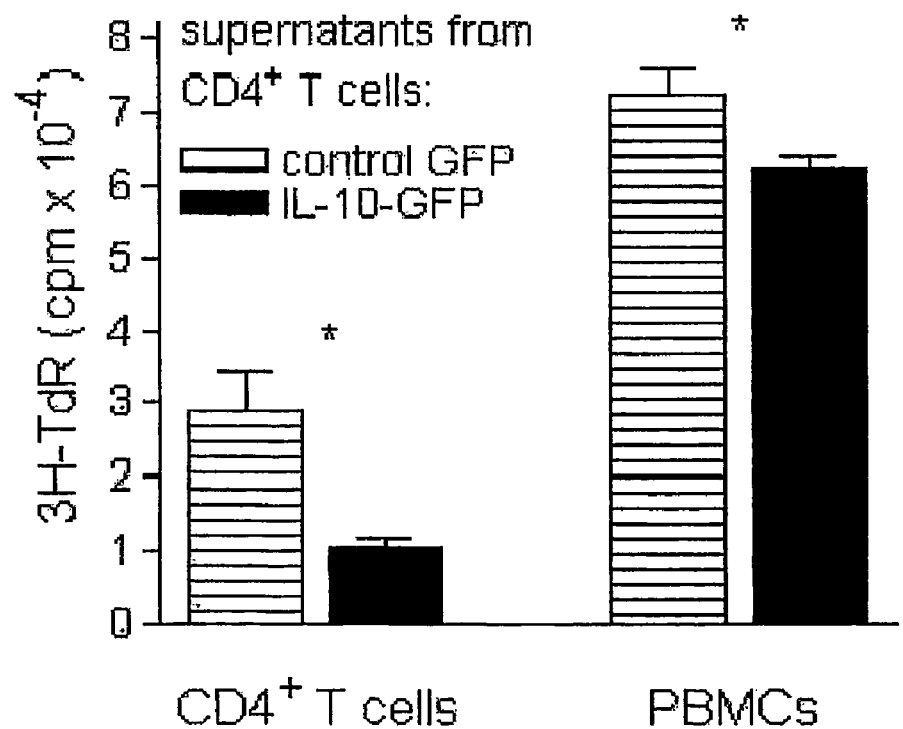
Figure 14C:
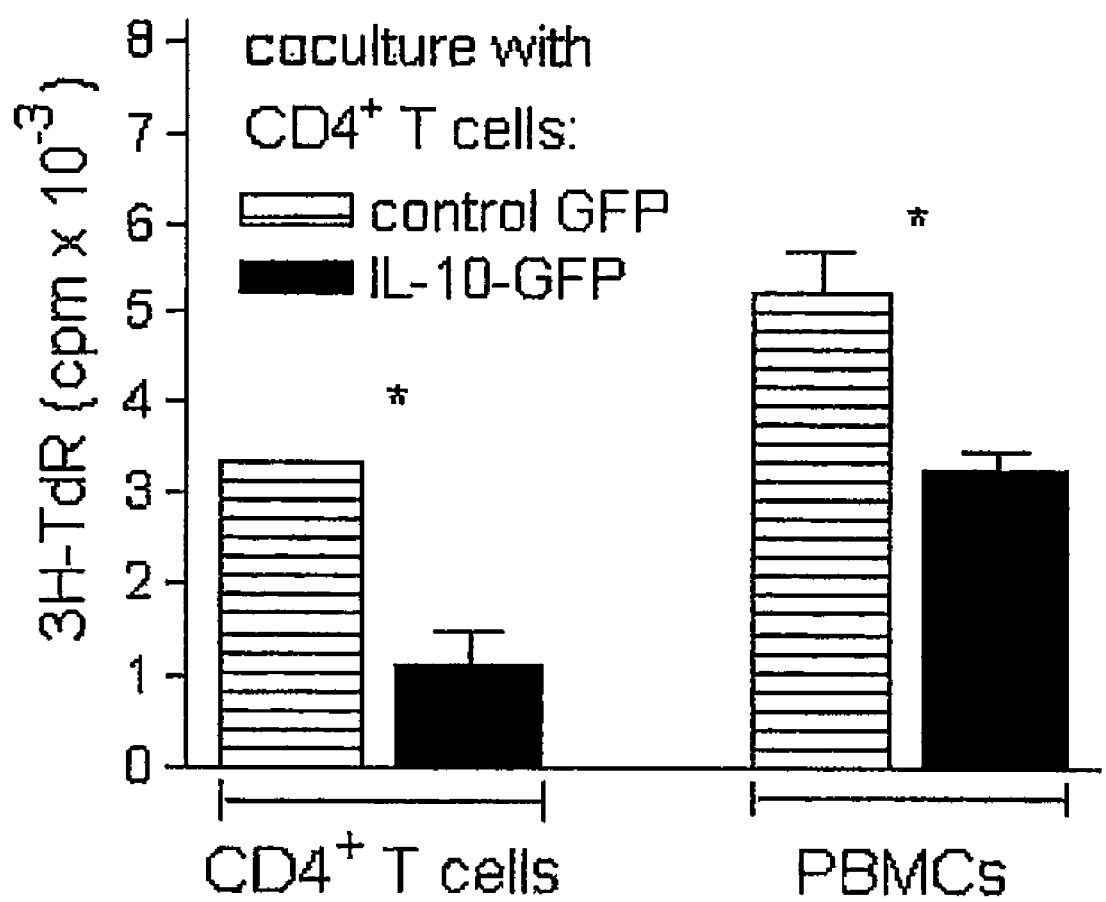

To obtain the effect of rIL-10 on alloantigen induced proliferation of responder cells (e.g. cultured CD4+ cells and fresh PBMCs), these cells were stimulated with purified allogeneic monocytes. In FIG. 14A, it is shown that rIL-10 inhibited the proliferative responses in a dose-dependent fashion. Significant inhibitory effects were already observed at rIL-10 concentrations of 1.25 ng/ml (p=0.049 versus no rIL-10 added) and 2.5 ng/ml p=0.050 versus no rIL-10 added) in the CD4+ cells and PBMCs, respectively. We compared this effect of rIL-10 with supernatants collected from IL-10-GFP or control GFP CD4+ cells after 48 h of αCD3/CD28 stimulation, containing IL-10 concentrations of 4.1±0.2 and 0.4±0.07 ng/ml, respectively. The supernatants from the IL-10-GFP CD4+ cells suppressed the proliferation of the autologous CD4+ cells and PBMC responder cells by an average of 61% and 18%, respectively (FIG. 14B). We next tested the ability of the transduced cells to suppress the proliferative responses of autologous responder cells to alloantigens in coculture experiments. Responder cells were stimulated with monocytes and different numbers of irradiated transduced cells. As shown in FIG. 14C at a ratio of 1:2 (IL-10-GFP CD4+ cells: responder cells), the proliferation of CD4+ cells and PBMCs was inhibited by an average of 67% and 38%, respectively. At a ratio of 1:1 the proliferative responses were even more reduced (data not shown) compared to the control GFP CD4+ cells. From this we conclude that the expression of the IL-10 transgene leads to secretion of IL-10 that is biologically active in both an autocrine and paracrine fashion.

2.2.4. IL-10-GFP CD4+ Cells Reduce IL-12 Production by Dendritic Cells

We next investigated whether interaction of the IL-10-GFP transduced CD4 cells with DCs influenced the capacity of DCs to produce IL-12, since it is known that rIL-10 suppresses IL-12 production by DCs.[60] should be [9] To this end, immature DCs were cocultured for 48 h with irradiated IL-10-GFP or control GFP CD4+ cells followed by thorough washing. DCs were incubated for another 24 h in the presence or absence of IFN-γ. In three independent experiments coculture of IL-10-GFP CD4+ cells with DCs resulted in a 8-fold decrease in IL-12p70 production (mean 79±21 pg/ml/24 h) compared to coculture with control GFP CD4+ cells (mean 436±75 pg/ml/24 h, p=0.004). DCs activated with IFN-γ also produced less IL-12p70 after coculture with IL-10-GFP CD4+ cells (162±46 versus 451±74, p=0.01).

These combined results indicate that the suppressive activities of IL-10-GFP CD4+ cells extend from CD4+ cells and monocytes to DCs.

2.2.5. Phenotype of IL-10 Transduced T Cells

We studied the cell surface phenotype of resting transduced cells by FACSscan analysis. As expected, MHC class II antigen was down-regulated on IL-10 transduced CD4+ cells (Table 3). On the other hand, IL-10-GFP transduction did not influence the expression of other activation markers (Table 3). CD154 (surface CTLA-4), important for down-regulation of activated CD4+ cells[61], was not detectable. Essentially all transduced CD4+ cells expressed the CD45RO marker of memory T cells.[62] Since the IL-10 transduced CD4+ cells should be specifically directed to the intestine after reinfusion to a patient, we studied the expression of different adhesion markers. The CD18, CD44, CD62L and α4β7 adhesion molecules direct lymphocytes respectively to inflammatory sites[63], high endothelial venules (HEV's)[64], peripheral lymph nodes[65], and to the intestine.[66] We observed an intermediate expression of CD62L (L-selectin) and high expression of CD18 (LFA-1) and CD44 on all transduced cells. Importantly, expression of the principal gut-homing molecule α4β7 was high on both transduced and non-transduced cultured CD4+ cells as compared to freshly isolated CD4+ cells (FIG. 15). The expression of the Th1 related molecule CXCR3[67] was comparable in both culture conditions.

TABLE 3

Phenotypic analysis of transduced CD4+ cells

| Marker | Antigen | Expression levels | |
| --- | --- | --- | --- |
| | | control GFP | IL-10-GFP |
| activation | MHC cl II | ++ | + |
| | CD25 | ± | ± |
| | CD27 | ± | ± |
| | CD152 | − | − |
| | CD154 | − | − |
| adhesion | CD18 | + | + |
| | CD44 | ++ | ++ |
| | CD62L | + | + |

Sorted GFP+CD4+ cells were stained with mAbs directly or indirectly labelled with PE or Cy as described in material and methods and analysed on a FACScan. Gates were set to contain live cells only. Indicated are the levels of expression (mean fluorescence intensity: MFI) in four categories as follows: MFI<10, −; MFI 10-200, ±; MFI 200-500, +; MFI>500, ++. The mean MFI of 2 donors (the same as used in FIG. 13) analysed in one experiment is shown and the results are representative for 8 donors.

2.2.6_α4β7 Mediates Adhesion of Transduced T Cells to MAdCAM-1

Since adhesion of gut-homing T cells to the intestinal HEV's depends on the expression of a functional form of α4β7 on the cell surface, we investigated whether adhesion of transduced CD4+ cells to MAdCAM-1 transfected 293T cells was α4β7-dependent. The GFP and IL-10-GFP CD4+ cells adhered more efficient to the MAdCAM-1 transfected cells than to control 293T cells (44% versus 26%, respectively). As shown in FIG. 16, adhesion of IL-10-GFP and control GFP CD4+ T cells to MAdCAM-1 transfected cells was partially blocked by pre-treatment with mAb against α4β7 or MAdCAM-1, but not by pretreatment with a control antibody. These results indicate that the expressed α4β7 mediated binding to MAdCAM-1, and T cells retain the capacity to bind to MAdCAM-1 after retroviral transduction.

LITERATURE

1. Groux H, O'Garra A, Bigler M, Rouleau M, Antonenko S, Devries J E, Roncarolo M G. A CD4+ T-cell subset inhibits antigen-specific T-cell responses and prevents colitis. *Nature* 1997; 389: 737-42.
2. Moore K W, A O G, de Waal Malefyt R, Vieira P, Mosmann T R. Interleukin-10. *Annu Rev Immunol* 1993; 11: 165-90.
3. Moore K W, de Waal Malefyt R, Coffman R L, O'Garra A. Interleukin-10 and the interleukin-10 receptor. *Annu Rev Immunol* 2001; 19: 683-765.
4. Levings M K, Sangregorio R, Galbiati F, Squadrone S, de Waal Malefyt R, Roncarolo M G. IFN-a and IL-10 induce the differentiation of human type 1 T regulatory cells. *J Immunol* 2001; 166: 5530-9.
5. Hagenbaugh A, Sharma S, Dubinett S M, Wei S H Y, Aranda R, Cheroutre H, Fowell D J, Binder S, Tsao B, Locksley R M, Moore K W, Kronenberg M. Altered immune responses in interleukin 10 transgenic mice. *J Exp Med* 1997; 185: 2101-10.
6. Asseman C, Mauze S, Leach M W, Coffman R L, Powrie F. An essential role for interleukin 10 in the function of regulatory T cells that inhibit intestinal inflammation. *J Exp Med* 1999; 190: 995-1004.
7. Berg D J, Davidson N, Kuhn R, Muller W, Menon S, Holland G, Thompson-Snipes L, Leach M W, Rennick D. Enterocolitis and colon cancer in interleukin-10-deficient mice are associated with aberrant cytokine production and CD4+ Th1-like responses. *J Clin Invest* 1996; 98: 1010-20.
8. Spencer S D, Di Marco F, Hooley J, Pitts-Meek S, Bauer M, Ryan A M, Sordat B, Gibbs V C, Aguet M. The orphan receptor CRF2-4 is an essential subunit of the interleukin 10 receptor. *J Exp Med* 1998; 187: 571-8.
9. Buelens C, Verhasselt V, De Groote D, Thielemans K, Goldman M, Willems F. Human dendritic cell responses to lipopolysaccharide and CD40 ligation are differentially regulated by interleukin-10. *Eur J Immunol* 1997; 27: 1848-52.
10. Davidson N J, Fort M M, Muller W, Leach M W, Rennick D M. Chronic colitis in IL-10$^{-/-}$ mice: insufficient counter regulation of a Th1 response. *Int Rev Immunol* 2000; 19: 91-121.
11. Fuss I J, Boirivant M, Lacy B, Strober W. The interrelated roles of TGF-b and IL-10 in the regulation of experimental colitis. *J Immunol* 2002; 168: 900-8.
12. Powrie F, Leach M W, Mauze S, Menon S, Caddle L B, Coffman R L. Inhibition of Th1 responses prevents inflammatory bowel disease in scid mice reconstituted with CD45RB$^{hi}$ CD4+ T cells. *Immunity* 1994; 1: 553-62.
13. Herfarth H H, Böcker U, Janardhanam R, Sartor R B. Subtherapeutic corticosteroids potentiate the ability of interleukin 10 to prevent chronic inflammation in rats. *Gastroenterology* 1998; 115: 856-65.
14. Fedorak R N, Gangl A, Elson C O, Rutgeerts P, Schreiber S, Wild G, Hanauer S, Kilian A, Cohard M, LeBeaut A, Feagan B, Group tIIBDCS. Recombinant human interleukin 10 in the treatment of patients with mild to moderately active Crohn's disease. *Gastroenterology* 2000; 119: 1473-82.
15. Schreiber S, Fedorak R N, Nielsen O H, Wild G, Williams N C, Nikolaus S, Jacyna M, Lashner B A, Gangl A, Rutgeerts P, Isaacs K, van Deventer S J H, Koningsberger J C, Cohard M, Lebaut A, Hanauer S B, group atCsdI-cs. Safety and efficacy of recombinant human interleukin 10 in chronic active Crohn's disease. *Gastroenterology* 2000; 119: 1461-72.
16. Colombel J F, Rutgeerts P, Malchow H, Jacyna M, Nielsen O H, Rask-Madsen J, Van Deventer S, Ferguson A, Desreumaux P, Forbes A, Geboes K, Melani L, Cohard M. Interleukin 10 (Tenovil) in the prevention of postoperative recurrence of Crohn's disease. *Gut* 2001; 49: 42-6.
17. Chernoff A E, Granowitz E V, Shapiro L, Vannier E, Lonnemann G, Angel J B, Kennedy J S, Rabson A R, Wolff S M, Dinarello C A. A randomized, controlled trial of IL-10 in humans. Inhibition of inflammatory cytokine production and immune responses. *J Immunol* 1995; 154: 5492-9.
18. Tilg H, van Montfrans C, van den Ende A, Kaser A, van Deventer S J H, Schreiber S, Gregor M, Rutgeerts P, Gasche C, Koningsberger J C, I. K, Cohard M, Lebeaut A, Grint P, and Weiss G. Treatment of Crohn's disease with recombinant human interleukin 10 induces the proinflammatory cytokine interfeon g. *GUT* 2002; 50: 191-5.
19. Mathisen P M, Yu M, Johnson J M, Drazba J A, Tuohy V K. Treatment of experimental autoimmune encephalomyelitis with genetically modified memory T cells. *J Exp Med* 1997; 186: 159-64.
20. Dal Canto R A, Shaw M K, Nolan G P, Steinman L, Fathman C G. Local delivery of TNF by retrovirus-transduced T lymphocytes exacerbates experimental autoimmune encephalomyelitis. *Clin Immunol* 1999; 90: 10-4.
21. Coligan J E, Kruisbeek A M, Margulies D H, Schevach E M, Strober W. Cytokines and their cellular receptors. Measurement of mouse and human interleukin 10. In: Coico R, ed. Current protocols in immunology: John Wiley & Sons, Inc., 2001: 614.
22. Anderson W F. Human gene therapy. *Nature* 1998; 392: 25-30.
23. Walther W, Stein U. Viral vectors for gene transfer—A review of their use in the treatment of human diseases. *Drugs* 2000; 60: 249-71.
24. Kay M A, Glorioso J C, Naldini L. Viral vectors for gene therapy: the art of turning infectious agents into vehicles of therapeutics. *Nat Med* 2001; 7: 33-40.
25. Russell W C. Update an adenovirus and its vectors. *J Gen Virol* 2000; 81: 2573-604.
26. Amado R G, Chen I S. Lentiviral vectors—the promise of gene therapy within reach? *Science* 1999; 285: 674-6.
27. Federico M. Lentiviruses as gene delivery vectors. *Curr Opin Biotechnol* 1999; 10: 448-53.
28. Vigiia E, Naldini L. Lentiviral vectors: excellent tools for experimental gene transfer and promising candidates for gene therapy. *J Gene Med* 2000; 2: 308-16.
29. Marin M, Noel D, Piechaczyk M. Towards efficient cell targeting by recombinant retroviruses. *Mol Med Today* 1997; 3: 396-403.
30. Peng K W, Russell S J. Viral vector targeting. *Curr Opin Biotechnol* 1999; 10: 454-7.
31. Sommerfelt M. Retrovirus receptors. *J Gen Virol* 1999; 80: 3049-64.
32. Gallardo H, Tan C, Ory D, Sadelain M. Recombinant retroviruses pseudotyped with the vesicular stomatitis virus G glycoprotein mediate both stable gene transfer and pseudotransduction in human peripheral blood lymphocytes. *Blood* 1997; 90: 952-7.
33. Reiser J. Production and concentration of pseudotyped HIV-1-based gene transfer vectors. *Gene Ther* 2000; 7: 910-3.
34. Lodge R, Subbramanian R A, Forget J, Lemay G, Cohen E A. MuLV-based vectors pseudotyped with truncated HIV glycoproteins mediate specific gene transfer in $CD4^+$ peripheral blood lymphocytes. *Gene Ther* 1998; 5: 655-64.
35. Miller A D, Garcia J V, von Shur N, Lynch C M, Wilson C, Eiden M V. Construction and properties of retrovirus packaging cells based on gibbon ape leukemia virus. *J Virol* 1991; 65: 2220-4.
36. Coligan J E, Kruisbeek A M, Margulies D H, Schevach E M, Strober W. Preparation of human mononuclear cell populations and subpopulations. In: Coico R, ed. Current protocols in immunology. Vol. 2: John Wiley & Sons, Inc., 1994:711-94.
37. Coligan J E, Kruisbeek A M, Margulies D H, Schevach E M, Strober W. Basis protocol: Isolation of mononuclear cells by Ficoll-Hypaque gradient centrifugation. In: Coico R, ed. Current protocols in immunology. Vol. 2: John Wiley & Sons, Inc., 1994:711-2.
38. Coligan J E, Kruisbeek A M, Margulies D H, Schevach E M, Strober W. Immunomagnetic purification of T cell subpopulations. In: Coico R, ed. Current protocols in immunology. Vol. 2: John Wiley & Sons, Inc., 1994:741-6.
39. Coligan J E, Kruisbeek A M, Margulies D H, Schevach E M, Strober W. Detection of unseparated human lymphocytes by flow cytometry. In: Coico R, ed. Current protocols in immunology. Vol. 2: John Wiley & Sons, Inc., 1994:791-4.
40. Coligan J E, Kruisbeek A M, Margulies D H, Schevach E M, Strober W. Isolation of monocyte/macrophage populations. In: Coico R, ed. Current protocols in immunology. Vol. 2: John Wiley & Sons, Inc., 1994:761-8.
41. Coligan J E, Kruisbeek A M, Margulies D H, Schevach E M, Strober W. Isolation and generation of human dendritic cells. In: Coico R, ed. Current protocols in immunology. Vol. 2: John Wiley & Sons, Inc., 1994:7321-73216.
42. Heemskerk M H M, Hooijberg E, Ruizendaal J J, van der Weide M M C, Kueter E, Bakker A Q, Schumacher T N M, Spits H. Enrichment of antigen-specific T cell response by retrovirally transduced human dendritic cells. *Cell Immunol* 1999; 195: 10-7.
43. Kinsella T M, Nolan G P. Episomal vectors rapidly and stably produce high-titer recombinant retrovirus. *Hum Gene Ylier* 1996; 7: 1405-13.
44. Vieira P, de Waal-Malefyt R, Dang M N, Johnson K E, Kastelein R, Fiorentino D F, de Vries J E, Roncarolo M G, Mosmann T R, Moore K W. Isolation and expression of human cytokine synthesis inhibitory factor cDNA clones: homology to Epstein-Barr virus open reading frame BCRFI. *Proc Natl Acad Sci USA* 1991; 88: 1172-6.
45. van Montfrans C, Hooijberg E, Rodriguez-Pena M S, Spits H, te Velde A A, van Deventer S J H. Generation of regulatory gut-homing human T lymphocytes using ex-vivo interleukin-10 gene transfer. submitted.
46. Powrie F, Read S. Induction of inflammatory bowel disease in immunodeficient mice by depletion of regulatory T cells. In: Coico R, ed. Current protocols in immunology. Vol. 4: John Wiley & Sons, Inc., 1999:15.3.1-0.3.0.
47. Ten Hove T, Corbaz A, Amitai H, Aloni S, Belzer I, Graber P, Drillenburg P, van Deventer S J, Chvatchko Y, Te Velde A A. Blockade of endogenous IL-18 ameliorates TNBS-induced colitis by decreasing local TNF-alpha production in mice. *Gastroenterology* 2001; 121: 1372-9.
48. Costa G L, Benson J M, Seroogy C M, Achacoso P, Fathmran C G, Nolan G P. Targeting rare populations of murine antigen-specific T lymphocytes by retroviral transduction for potential application in gene therapy for autoinmuune disease. *J Immunol* 2000; 164: 3581-90.
49. Marx J C, Allay J A, Persons D A, Nooner S A, Hargrove P W, Kelly P F, Vanin E F, Horwitz E M. High-efficiency transduction and long-term gene expression with a murine stem cell retroviral vector encoding the green fluorescent protein in human marrow stromal cells. Hum Gene Ther 1999; 10: 1163-73.
50. Powrie F, Leach M W, Mauze S, Caddle L B, Coffman R L. Phenotypically distinct subsets of $CD4^+$ T cells induce or protect from chronic intestinal inflammation in C. B-17 scid mice. *Int Immunol* 1993; 5: 1461-71.
51. Rudolphi A, Boll G, Poulsen S S, Claesson M H, Reimann J. Gut-homing CD4+ T cell receptor alpha beta+ T cells in the pathogenesis of murine inflammatory bowel disease. *Eur J Immunol* 1994; 24: 2803-12.
52. Aranda R, Sydora B C, McAllister P L, Binder S W, Yang H Y, Targan S R, Kronenberg M. Analysis of intestinal lymphocytes in mouse colitis mediated by transfer of CD4+, $CD45RB^{high}$ T cells to SCID recipients. *J Immunol* 1997; 158: 3464-73.
53. Spits H, Keizer G, Borst J, Terhorst C, Hekinan A, de Vries J E. Characterization of monoclonal antibodies against cell surface molecules associated with cytotoxic activity of natural and activated killer cells and cloned CTL lines. *Hybridoma* 1983; 2: 423-37.
54. Sallusto F, Lanzavecchia A. Efficient presentation of soluble antigen by cultured human dendritic cells is maintained by granulocyte/macrophage colony-stimulating factor plus interleukin 4 and downregulated by tumor necrosis factor alpha. *J Exp Med* 1994; 179: 1109-18.
55. Kalinski P, Schuitemaker J H, Hilkens C M, Kapsenberg M L. Prostaglandin E2 induces the final maturation of 56. Hooijberg E, Ruizendaal J J, Snijders P J F, Kueter E W M, Walboomers J M M, Spits H. Immortalization of human CD8+ T cell clones by ectopic expression of telomerase reverse transcriptase. *J Immunol* 2000; 165.
57. Pollok K E, van der Loo J C, Cooper R J, Kennedy L, Williams D A. Costimulation of transduced T lymphocytes via T cell receptor-CD3 complex and CD28 leads to increased transcription of integrated retrovirus. *Hum Gene Ther* 1999; 10: 2221-36.
58. de Waal Malefyt R, Yssel H, de Vries J E. Direct effects of IL-10 on subsets of human CD4+ T cell clones and resting T cells. Specific inhibition of IL-2 production and proliferation. *J Immunol* 1993; 150: 4754-65.
59. Taga K, Mostowski H, Tosato G. Human interleukin-10 can directly inhibit T-cell growth. *Blood* 1993; 81: 2964-71.
60. Buelens C, Verhasselt V, De Groote D, Thielemans K, Goldman M, Willems F. Interleulcin-10 prevents the generation of dendritic cells from human peripheral blood mononuclear cells cultured with interleukin-4 and granulocyte/macrophage-colony-stimulating factor. *Eur J Immunol* 1997; 27: 756-62.
61. Chambers C A, Allison J P. Costimulatory regulation of T cell function. *Curr Opin Cell Biol* 1999; 11: 203-10.
62. Dutton R W, Bradley L M, Swain S L. T cell memory. *Annu Rev Immunol* 1998; 16: 201-23.
63. Springer T A. Adhesion receptors of the immune system. *Nature* 1990; 346: 425-34.
64. Haynes B F, Telen M J, Hale L P, Denning S M. CD44-a molecule involved in leukocyte adherence and T-cell activation. *Immunol Today* 1989; 10: 423-8.
65. Picker L J, Treer J R, Ferguson-Darnell B, Collins P A, Buck D, Terstappen L W. Control of lymphocyte recirculation in man. I. Differential regulation of the peripheral lymph node homing receptor L-selection on T cells during the virgin to memory cell transition. *J Immunol* 1993; 150: 1105-21.
66. Erle D J, Briskin M J, Butcher E C, Garcia-Pardo A, Lazarovits A I, Tidswell M. Expression and function of the MAdCAM-1 receptor, integrin alpha 4 beta 7, on human leukocytes. *J Immunol* 1994; 153: 517-28.
67. Sallusto F, Lanzavecchia A, Mackay C R. Chemokines and chemokine receptors in T-cell priming and Th1/Th2-mediated responses. *Immunol Today* 1998; 19: 568-75.

The invention claimed is:

1. A method for producing an anti-inflammatory, antigen-non-specific population of lymphocytes overexpressing interleukin-10 (IL-10) polypeptide that are useful for treating a Th1-mediated inflammatory disease in an antigen-independent manner when administered to a subject, the method comprising:
   (a) modifying at least a portion of a peripheral blood mononuclear cell population from a healthy donor, among which cells lymphocytes are not selected or enriched on the basis of antigen specificity, by introducing into said cells an expression construct that comprises a nucleotide sequence encoding an IL-10 polypeptide; and,
   (b) recovering, from said modified mononuclear cells, lymphocytes or a subset thereof that overexpress the IL-10 polypeptide,
thereby producing said anti-inflammatory, antigen non-specific lymphocyte population.

2. A method according to claim 1, wherein prior to the introducing of step (a), the cells are induced to, or allowed to, proliferate.

3. A method according to claim 2, wherein the cells are induced to proliferate by exposure to a proliferating agent.

4. A method according to claim 3, wherein the proliferating agent is one or more of
   (a) an anti-CD3 antibody;
   (b) an anti-CD28 antibody; or
   (c) phytohemagglutinin.

5. A method according to claim 1, wherein prior to or subsequent to step (a), the mononuclear cells are fractionated to yield an enriched fraction or subset of lymphocytes.

6. A method for producing a pharmaceutical composition comprising lymphocytes overexpressing IL-10, which method comprises
   (a) producing the lymphocytes overexpressing IL-10 in accordance with claim 1, and
   (b) combining said lymphocytes with an acceptable pharmaceutical carrier.

7. The method according to claim 1 wherein the lymphocyte subset comprises an enriched population of B lymphocytes or T lymphocytes.

8. The method according to claim 7, wherein the lymphocyte subset comprises an enriched population of T lymphocytes.

9. The method according to claim 8 wherein the T lymphocytes are CD4+ T lymphocytes.

10. A composition comprising lymphocytes from a healthy donor that are:
    (i) not selected to be specific for a predetermined antigen, and
    (ii) which cells are modified to comprise and overexpress an IL-10 transgene.

11. The composition according to claim 10 wherein the lymphocytes are T lymphocytes.

12. A T lymphocyte composition according to claim 11, wherein the T cells functionally mimic regulatory T cells in that they inhibit:
    (a) proliferation of autologous responder cells, and/or
    (b) production of pro-inflammatory cytokine IL-12 by dendritic cells.

13. A pharmaceutical composition comprising the composition according to claim 11, and a pharmaceutically acceptable carrier.

14. A method of treating a Th1-mediated inflammatory disease or condition associated with undesired activation and/or expansion of T cells in a subject in need thereof, comprising administering an effective amount of a pharmaceutical composition according to claim 13 to said subject.

15. A composition according to claim 11 wherein the T lymphocytes are CD4+ T lymphocytes.

16. A pharmaceutical composition comprising the composition according to claim 15, and a pharmaceutically acceptable carrier.

17. A method of treating a Th1-mediated inflammatory disease or condition associated with undesired activation and/or expansion of T cells in a subject in need thereof, comprising administering an effective amount of a pharmaceutical composition according to claim 16 to said subject.

18. A pharmaceutical composition comprising the composition according to claim 10, and a pharmaceutically acceptable carrier.

19. A method of treating a Th1-mediated inflammatory disease or condition associated with undesired activation and/or expansion of T cells in a subject in need thereof, comprising administering an effective amount of a pharmaceutical composition according to claim 18 to said subject.

20. The method according to claim 19, wherein the Th1-mediated inflammatory disease or condition is Crohn's disease, reactive arthritis, insulin-dependent diabetes, colitis, pancreatitis, an inflammatory lung disease, an inflammatory eye disease, multiple sclerosis, Hashimoto's thyroiditis, Graves' disease, chronic articular rheumatism, contact dermatitis, psoriasis, graft rejection, graft-versus-host disease, or sarcoidosis.

21. The method according to claim 20 wherein the Th1-mediated inflammatory disease Crohn's disease or colitis.

* * * * *